US011517581B2

(12) United States Patent
Yuan et al.

(10) Patent No.: US 11,517,581 B2
(45) Date of Patent: Dec. 6, 2022

(54) ZIKA VIRUS PROTEASE INHIBITORS AND METHODS OF USE THEREOF

(71) Applicants: VERSITECH LIMITED, Hong Kong (CN); FUNDACION UNIVERSITARIA SAN ANTONIO, Murcia (ES)

(72) Inventors: Shuofeng Yuan, Hong Kong (CN); Fuk Woo Jasper Chan, Hong Kong (CN); Kwok Yung Yuen, Hong Kong (CN); Helena Den Haan, Murcia (ES); Jorge Pena-García, Murcia (ES); José Pedro Cerón-Carrasco, Murcia (ES); Horacio Emilio Pérez-Sánchez, Murcia (ES)

(73) Assignees: VERSITECH LIMITED, Hong Kong (CN); FUNDACION UNIVERSITARIA SAN ANTONIO, Murcia (ES)

( * ) Notice: Subject to any disclaimer, the term of this patent is extended or adjusted under 35 U.S.C. 154(b) by 397 days.

(21) Appl. No.: 16/606,877

(22) PCT Filed: Jun. 15, 2017

(86) PCT No.: PCT/CN2017/088420
§ 371 (c)(1),
(2) Date: Oct. 21, 2019

(87) PCT Pub. No.: WO2018/192083
PCT Pub. Date: Oct. 25, 2018

(65) Prior Publication Data
US 2020/0384005 A1    Dec. 10, 2020

Related U.S. Application Data

(60) Provisional application No. 62/487,856, filed on Apr. 20, 2017, provisional application No. 62/491,007, filed on Apr. 27, 2017.

(51) Int. Cl.
*A61K 31/7048* (2006.01)
*A61K 38/095* (2019.01)
*A61P 31/14* (2006.01)
*C12Q 1/37* (2006.01)

(52) U.S. Cl.
CPC ........ *A61K 31/7048* (2013.01); *A61K 38/095* (2019.01); *A61P 31/14* (2018.01); *C12Q 1/37* (2013.01); *G01N 2333/9513* (2013.01)

(58) Field of Classification Search
None
See application file for complete search history.

(56) References Cited

U.S. PATENT DOCUMENTS

2018/0127800 A1* 5/2018 Wolkowicz ............ C12Q 1/37
2021/0052621 A1* 2/2021 Rana .................... A61K 31/341

FOREIGN PATENT DOCUMENTS

CN    106511346 A    3/2017

OTHER PUBLICATIONS

International Search Report dated Mar. 21, 2018 in International Application No. PCT/CN2017/088420.
Chan, J.F.W. et al., "Zika fever and congenital Zika syndrome: An unexpected emerging arboviral disease", Journal of Infection, 2016, 72:507-524, The British Infection Association.
Duffy, M.R. et al., "Zika Virus Outbreak on Yap Island, Federated States of Micronesia", The New England Journal of Medicine, Jun. 11, 2009, 360(24):2536-2543, Massachusetts Medical Society.
Arzuza-Ortega, L. et al., "Fatal Sickle Cell Disease and Zika Virus Infection in Girl from Colombia", Emerging Infectious Diseases, May 2016, 22(5):925-927.
Azevedo, R.S.S. et al., "Zika virus epidemic in Brazil. I. Fatal disease in adults: Clinical and laboratorial aspects", J. Clin. Virol., Dec. 2016, 85:56-64.
Cao-Lormeau, V.M. et al., "Guillain-Barré Syndrome outbreak caused by Zika virus infection in French Polynesia", Lancet., Apr. 9, 2016, 387(10027):1531-1539.
Carteaux, G. et al., "Zika Virus Associated with Meningoencephalitis", The New England Journal of Medicine, Apr. 21, 2016, vol. 374, No. 16, 4 pages, Massachusetts Medical Society.
Chraïbi, S. et al., "Two cases of thrombocytopenic purpura at onset of Zika virus infection", Journal of Clinical Virology, 2016, 83:61-62, Elsevier B.V.
Mécharles, S. et al., "Acute myelitis due to Zika virus infection", Lancet, Apr. 2, 2016, 387:1481.
Sarmiento-Ospina, A. et al., "Zika virus associated deaths in Colombia", Lancet Infect. Dis., May 2016, 16:523-524.
Soares, C.N. et al., "Fatal encephalitis associated with Zika virus infection in an adult", Journal of Clinical Virology, 2016, 83:63-65, Elsevier B.V.
Chan, J.F.W. et al., "Zika Virus Infection in Dexamethasone-immunosuppressed Mice Demonstrating Disseminated Infection with Multi-organ Involvement Including Orchitis Effectively Treated by Recombinant Type I Interferons", EBioMedicine, 2016, 14:112-122, Elsevier B.V.
Foy, B.D. et al., "Probable Non-Vector-borne Transmission of Zika Virus, Colorado, USA", Emerg. Infect. Dis., May 2011, 7 pages.
Govero, J. et al., "Zika virus infection damages the testes in mice", Nature, Dec. 15, 2016, 540(7633):438-442.
Ma, W. et al., "Zika Virus Causes Testis Damage and Leads to Male Infertility in Mice", Cell, Dec. 1, 2016, 167:1511-1524, Elsevier Inc.
Musso, D. et al., "Potential Sexual Transmission of Zika Virus", Emerging Infectious Diseases, Feb. 2015, 21 (2):359-361.
Barrows, N.J. et al., "A Screen of FDA-Approved Drugs for Inhibitors of Zika Virus Infection", Cell Host & Microbe, Aug. 10, 2016, 20:259-270, Elsevier Inc.

(Continued)

Primary Examiner — Traviss C McIntosh, III
(74) Attorney, Agent, or Firm — Maier & Maier, PLLC

(57) ABSTRACT

Methods and compounds for preventing and/or treating Zika virus (ZIKA) infection. And methods to screen for compound to prevent or treat Zika virus infection.

9 Claims, 11 Drawing Sheets

(56) References Cited

OTHER PUBLICATIONS

Retallack, H. et al., "Zika virus cell tropism in the developing human brain and inhibition by azithromycin", PNAS, Dec. 13, 2016, 113(50):14408-14413.
Xu, M. et al., "Identification of small-molecule inhibitors of Zika virus infection and induced neural cell death via a drug repurposing screen", Nature Medicine, Oct. 2016, 22(10):1101-1109, Nature America, Inc.
Lei, J. et al., "Crystal structure of Zika virus NS2B-NS3 protease in complex with a boronate inhibitor", Science, Jul. 29, 2016, 353(6298):503-505, American Association for the Advancement of Science.
Halgren, T.A., "Potential energy functions", Current Opinion in Structural Biology, 1995, 5:205-210, Current Biology Ltd ISSN 0959-440X.
Sastry, G.M. et al., "Protein and ligand preparation: parameters, protocols, and influence on virtual screening enrichments", J. Comput Aided Mol Des, 2013, 27:221-234, Springer Science+Business Media Dordrecht 2013.
Stroganov, O.V. et al., Lead Finder: An Approach to Improve Accuracy of Protein—Ligand Docking, Binding Energy Estimation, and Virtual Screening, J. Chem. Inf. Model., 2008, 48:2371-2385, American Chemical Society.
Shivakumar, D. et al., "Prediction of Absolute Solvation Free Energies using Molecular Dynamics Free Energy Perturbation and the OPLS Force Field", J. Chem. Theory Comput., 2010, 6:1509-1519, American Chemical Society.
Chan, J.F.W. et al., "Differential cell line susceptibility to the emerging Zika virus: implications for disease pathogenesis, non-vector-borne human transmission and animal reservoirs", Emerging Microbes & Infections, 2016, 5(e93):1-12.
Zhou, J. et al., "Active Replication of Middle East Respiratory Syndrome Coronavirus and Aberrant Induction of Inflammatory Cytokines and Chemokines in Human Macrophages: Implications for Pathogenesis", MERS-CoV in Macrophages and Pathogenesis, JID 2014:209, May 1, 2014, pp. 1331-1342.
Chan, J.F.W. et al., "Differential Cell Line Susceptibility to the Emerging Novel Human Betacoronavirus 2c EMC/2012: Implications for Disease Pathogenesis and Clinical Manifestation", Cell Line Susceptibility to HCoV-EMC, JID 2013:207, Jun. 1, 2013, pp. 1743-1752.
Chan, J.F.W. et al., "Novel antiviral activity and mechanism of bromocriptine as a Zika virus NS2B-NS3 protease inhibitor", Antiviral Research, 2017, 141:29-37, Elsevier B.V.
Yuan, S. et al., "A novel small-molecule compound disrupts influenza A virus PB2 cap-binding and inhibits viral replication", Journal of Antimicrobial Chemotherapy, 2016, 71:2489-2497.
Kato, F. et al., "Novel antiviral activity of bromocriptine against dengue virus replication", Antiviral Research, 2016, 131:141-147, Elsevier B.V.
Chan, J.F.W. et al., "Improved detection of Zika virus RNA in human and animal specimens by a novel, highly sensitive and specific real-time RT-PCR assay targeting the 5'-untranslated region of Zika virus", Tropical Medicine and International Health, May 2017, 22(5):594-603, John Wiley & Sons Ltd.
Wishart, D.S. et al., "DrugBank: a comprehensive resource for in silico drug discovery and exploration", Nucleic Acids Research, 2006, vol. 34, Database issue, pp. D668-D672, Oxford University Press.

Phoo, W.W. et al., "Structure of the NS2B-NS3 protease from Zika virus after self-cleavage", Nature Communications, Nov. 15, 2016, vol. 7:13410, pp. 1-8.
Zmurko, J. et al., "The Viral Polymerase Inhibitor 7-Deaza-2'-C-Methyladenosine Is a Potent Inhibitor of In Vitro Zika Virus Replication and Delays Disease Progression in a Robust Mouse Infection Model", PLOS, May 10, 2016, pp. 1-15.
Kirby, W.M.M. et al., "Clinical and Laboratory Studies of Novobiocin, a New Antibiotic", A.M.A. Archives of Internal Medicine, 1956, pp. 1-7.
Civitico, G. et al., "Antiviral Strategies in Chronic Hepatitis B Virus Infection: II. Inhibition of Duck Hepatitis B Virus In Vitro Using Conventional Antiviral Agents and Supercoiled-DNA Active Compounds", Journal of Medical Virology, 1990, 31:90-97, Wiley-Liss, Inc.
Dröge, P. et al., "Inhibition of DNA synthesis by aphidicolin induces supercoiling in simian virus 40 replicative intermediates", The EMBO Journal, 1985, 4(12):3241-3246, IRL Press Limited, Oxford, England.
Furlini, G. et al., "In-vivo effect of novobiocin on primary cytomegalovirus infection", Journal of Antimicrobial Chemotherapy, 1983, 12:503-506, The British Society for Antimicrobial Chemotherapy.
González-Molleda, L. et al., "Potent Antiviral Activity of Topoisomerase I and II Inhibitors against Kaposi's Sarcoma-Associated Herpesvirus", Antimicrobial Agents and Chemotherapy, pp. 893-902, American Society for Microbiology.
Pessina, A. et al., "Lack of in vitro antiviral activity of fluoroquinolones against herpes simplex virus type 2", Archives of Virology, 1992, 122:263-269, Springer-Verlag.
Sekiguchi, J. et al., "Novobiocin Inhibits Vaccinia Virus Replication by Blocking Virus Assembly", Virology, 1997, 235:129-137, Academic Press.
Wu, T. et al., "Antiviral activity of topoisomerase II catalytic inhibitors against Epstein-Barr virus", Antiviral Research, 2014, 107:95-101, Elsevier B.V.
Zhu, Z. et al., "Comparative genomic analysis of pre-epidemic and epidemic Zika virus strains for virological factors potentially associated with the rapidly expanding epidemic", Emerging Microbes and Infections, 2016, 5(e22):1-11.
Drusano, G.L. et al., "Steady-State Serum Pharmacokinetics of Novobiocin and Rifampin Alone and in Combination", Antimicrobial Agents and Chemotherapy, Jul. 1986, 30(1):42-45, American Society for Microbiology.
Zhang, X. et al., "Significantly enhanced bioavailability of niclosamide through submicron lipid emulsions with or without PEG-lipid: a comparative study", Journal of Microencapsulation, 2015, 32(5):496-502, Informa UK Ltd.
Case, D.A. et al., "Amber2017 Reference Manual (Covers Amber16 and AmberTools17)", 951 pages.
Delvecchio, R. et al., "Chloroquine, an Endocytosis Blocking Agent, Inhibits Zika Virus Infection in Different Cell Models", Viruses, 2016, 8(322):1-15.
Musso, D. et al., "Zika Virus", Clinical Microbiology Reviews, Jul. 2016, 29(3):478-524, American Society for Microbiology.
Bullard-Feibelman, K.M. et al., "The FDA-approved Drug Sofosbuvir Inhibits Zika Virus Infection", Antiviral Res., Jan. 2017, 137:134-140.
Chan, J.F.W. et al., "Broad-spectrum antivirals for the emerging Middle East respiratory syndrome coronavirus", Journal of Infection, 2013, 67:606-616, The British Infection Association.

\* cited by examiner

Figure 1

In silico structure-based virtual screening: identification of top 100 primary hit compounds (100 / 8277)

Primary screening: selection of 8 clinically approved drugs belonging to different drug classes for further validation studies (8 / 100)

Validation of protease inhibition: ZIKV-NS2B-NS3 fluorescence-based protease inhibition assay (5 / 8)

Validation of in vitro anti-ZIKV activity: further selection of 3 validated ZIKV-NS2B-NS3 protease inhibitors that have high potentials for clinical use (2 / 3)

Validation of in vivo anti-ZIKV activity: selection of novobiocin for evaluation in mouse model based on its optimal pharmacological properties (1 / 3)

ZIKA VIRUS PROTEASE INHIBITORS AND METHODS OF USE THEREOF

CROSS-REFERENCE TO RELATED APPLICATIONS

This application is the U.S. national stage application of International Patent Application No. PCT/CN2017/088420, filed Jun. 15, 2017, which claims the benefit of U.S. Provisional Application Nos. 62/487,856, filed Apr. 20, 2017, and 62/491,007, filed Apr. 27, 2017, the disclosure of each of which is incorporated herein by reference in its entirety.

FIELD OF THE INVENTION

The disclosed invention is generally in the field of virology and specifically in the area of Zika virus.

BACKGROUND OF THE INVENTION

Zika virus (ZIKV) is an emerging human pathogenic flavivirus that is spread mostly by the bite of an infected *Aedes aegypti* or *Aedes albopictus* mosquito. Although historically transmission of ZIKV was limited mainly to the southern hemisphere, recent changes in climate have caused the virus to spread further north, with more and more reports of sustained transmission in the continental United States. The ability of the virus to be passed from pregnant women to their fetuses is well documented. Consequently, ZIKV has caused an unprecedented large-scale epidemic of congenital microcephaly and malformations in the Americas (Chan et al., J. Infect. 72, 507-524 (2016a)).

Symptoms of acute ZIKV infection include fever, rash, headache, joint pain, conjunctivitis, and muscle pain. Although the illness was initially thought to be completely self-limiting in infected adults, an increasing number of serious complications were recently reported among adult patients as the epidemic expanded in the Americas and other regions (Duffy et al., N. Engl. J. Med. 360, 2536-2543 (2009); Musso and Gubler, Clin. Microbiol. Rev. 29, 487-524 (2016)). These included severe neurological complications, such as Guillain-Barré syndrome, meningoencephalitis, and myelitis, thrombocytopenia and disseminated intravascular coagulation with hemorrhagic complications, hepatic dysfunction, acute respiratory distress syndrome, shock, multi-organ dysfunction syndrome, and death (Arzuza-Ortega et al., Emerg. Infect. Dis. 22, 925-927 (2016); Azevedo et al., J. Clin. Virol. 85, 56-64 (2016); Cao-Lormeau et al., Lancet 387, 1531-1539 (2016); Carteaux et al., N. Engl. J. Med. 374, 1595-1596 (2016); Chraibi et al., J. Clin. Virol. 83, 61-62 (2016); Mecharles et al., Lancet 387, 1481 (2016); Sarmiento-Ospina et al., Lancet Infect. Dis. 16, 523-524 (2016); Soares et al., J. Clin. Virol. 83, 63-65 (2016)). Alarmingly, human cases of hematospermia and mouse models of orchitis with possible long-term effects on male fertility were also described (Chan et al., EBioMedicine 14, 112-122 (2016c); Foy et al., Emerg. Infect. Dis. 17, 880-882 (2011); Govero et al., Nature 540, 438-442 (2016); Ma et al., Cell 167, 1511-24.e10 (2016); Musso et al., Emerg. Infect. Dis. 21, 359-361 (2015)).

Current methods for preventing ZIKV infection include prevention of mosquito bites by wearing long-sleeved shirts and pants, staying indoors, using window and door screens, and use of pesticides and insect repellents. It is also generally recommended that sexual transmission of the virus be prevented by use of condoms.

As there are currently no vaccines or drugs specifically tailored to ZIKV infection, current methods and recommendations for treatment consist mostly of supportive care. These methods include getting rest, drinking fluids to prevent dehydration, and taking over-the-counter drugs such as acetaminophen to reduce pain and fever. Treatment options for ZIKV infection in pregnant patients and severe ZIKV-associated complications remain particularly limited.

To identify immediately available anti-ZIKV treatment options, a number of drug repurposing programs have been conducted by screening drug libraries using cell culture-based antiviral assays (Barrows et al., Cell Host Microbe 20, 259-270 (2016); Retallack et al., Proc. Natl. Acad. Sci. U.S.A. 113, 14408-14413 (2016); Xu et al., Nature Med. 22, 1101-1107 (2016)). However, most of these clinically approved drugs found to have in vitro anti-ZIKV activity are anti-cancer or immunomodulating agents which are immunosuppressive or contraindicated in pregnancy (FDA pregnancy category D). Moreover, such screening approaches do not elucidate the anti-ZIKV mechanisms of these drugs, which are important for further development of safer and more effective drug analogues of the leading drug compounds. Alternative approaches to preventing and treating Zika virus infection are needed, in particular in view of its effects on developing fetuses.

It is therefore an object of the present invention to provide compounds that can prevent or treat Zika virus infection with fewer toxic effects on the patient.

It is a further object of the present invention to provide methods that can prevent or treat Zika virus infection with fewer toxic effects on the patient.

It is a further object of the present invention to provide methods for identifying or selecting compounds that can prevent or treat Zika virus infection with fewer toxic effects on the patient.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise," or variations such as "comprises" or "comprising," will be understood to imply the inclusion of a stated element, integer or step, or group of elements, integers or steps, but not the exclusion of any other element, integer or step, or group of elements, integers or steps.

BRIEF SUMMARY OF THE INVENTION

Disclosed are methods and compounds to prevent or treat Zika virus (ZIKV) infection. Disclosed are materials and methods of preventing and/or treating ZIKV infection. In some forms, disclosed is a method for preventing and/or treating ZIKV infection in a subject, the method comprising diagnosing the subject as suffering from, or being at risk of developing, ZIKV infection; and administering to the subject an effective amount of a composition that prevents and/or treats the ZIKV infection. In some forms, the composition can comprise an effective amount of a compound selected from novobiocin, lopinavir-ritonavir, rifampicin, desmopressin acetate, and octreotide acetate. Also disclosed are methods for identifying compounds that are useful for the prevention and/or treatment of ZIKV infection, the methods comprising structural screening of known drug candidates and evaluation using in vitro and in vivo ZIKV infection models.

Disclosed are methods for preventing or treating Zika virus infection where the method involves administering, to a subject suffering from, or being at risk of developing, Zika virus infection, an effective amount of a composition that inhibits Zika virus protease. As another example, disclosed are methods for preventing and/or treating Zika virus infection in a subject where the method involves diagnosing the subject as suffering from, or being at risk of developing, Zika virus infection; and administering to the subject an effective amount of a composition that prevents and/or treats the Zika virus infection.

In some forms, the amount of the composition is effective to inhibit Zika virus protease in the subject. In some forms, the subject is an adult. In some forms, the subject is pregnant. In some forms, the subject is immune compromised. An immune compromised subject is generally considered to be in a state in which the immune system's ability to fight infectious disease and cancer is compromised or entirely absent.

In some forms, the composition includes novobiocin, lopinavir-ritonavir, rifampicin, desmopressin acetate, octreotide acetate, or a combination thereof. In some forms, the composition includes novobiocin, lopinavir-ritonavir, or combinations thereof. In some forms, the composition includes novobiocin. In some forms, the composition includes an effective amount of novobiocin. In some forms, the effective amount of novobiocin is less than 300 mg/kg/d.

In some forms, the method further involves, prior to administering, diagnosing the subject as suffering from, or being at risk of developing, Zika virus infection. In some forms, the subject is at risk of developing Zika virus infection. In some forms, the amount of the composition administered to the subject at risk of Zika virus infection is an amount effective to prevent Zika virus infection in the subject.

In some forms, the subject is suffering from Zika virus infection. In some forms, the amount of the composition administered to the subject suffering from Zika virus infection is an amount effective to treat the Zika virus infection in the subject.

Also disclosed are methods to identify compounds useful for preventing or treating Zika virus infection. For example, disclosed are methods for identifying a compound that inhibits Zika virus protease where the method involves (a) bringing into contact, in a first test chamber, a protease substrate, a test compound, and a Zika virus isolate comprising at least one Zika virus protease, and (b) measuring the amount of the protease substrate that is cleaved in the first test chamber. In some forms, the test compound can be identified as a compound that inhibits Zika virus protease if the measured amount of cleaved protease substrate in the first test chamber is less than the amount of cleaved protease substrate measured in a control test chamber having no test compound.

In some forms, steps (a) and (b) can be performed in one or more additional test chambers, each having an amount of the test compound different from the amount of test compound in the first test chamber. In some forms, the test compound can be identified as a compound that inhibits Zika virus protease if the measured amount of cleaved protease substrate in one of the test chambers having less than 50 μg/ml of the test compound is at least 50% less than the amount of cleaved protease substrate measured in the control test chamber.

In some forms, the first test chamber can have less than 50 μg/ml of the test compound. In some forms, the test compound can be identified as a compound that inhibits Zika virus protease if the measured amount of cleaved protease substrate in the first test chamber is at least 50% less than the amount of cleaved protease substrate measured in the control test chamber.

In some forms, the test compound can be a compound identified as a compound that is predicted to form a stable complex with a Zika virus protease using molecular dynamics simulations. In some forms, the molecular dynamics simulations can use a protein model system built using the crystal structure of a Zika virus protease and the structure of candidate compounds.

Also disclosed are methods for identifying a compound that inhibits Zika virus infection where the method involves (a) bringing into contact, in a first test chamber, a Zika virus-susceptible cell line, a test compound, and a Zika virus isolate, and (b) measuring the level of a cytopathic effect of the Zika virus isolate on the Zika virus-susceptible cell line in the first test chamber. In some forms, the test compound can be identified as a compound that inhibits Zika virus infection if the measured level of the cytopathic effect in the first test chamber is less than the level of the cytopathic effect measured in a control test chamber having no test compound.

In some forms, steps (a) and (b) can be performed in one or more additional test chambers, each having an amount of the test compound different from the amount of test compound in the first test chamber. In some forms, the test compound can be identified as a compound that inhibits Zika virus infection if the measured level of the cytopathic effect in one of the test chambers having less than 50 μg/ml of the test compound is at least 50% less than the level of the cytopathic effect measured in the control test chamber.

In some forms, the first test chamber can have less than 50 μg/ml of the test compound. In some forms, the test compound can be identified as a compound that inhibits Zika virus infection if the measured level of the cytopathic effect in the first test chamber is at least 50% less than the level of the cytopathic effect measured in the control test chamber.

In some forms, the test compound can be a compound identified as a compound that is predicted to form a stable complex with a Zika virus non-structural protein using molecular dynamics simulations. In some forms, the molecular dynamics simulations can use a protein model system built using the crystal structure of a Zika virus non-structural protein and the structure of candidate compounds.

Also disclosed are methods for identifying compounds that are useful for the prevention and/or treatment of Zika virus infection where the method involves providing a protease substrate, providing candidate drug compounds, providing a Zika virus isolate comprising at least one Zika virus protease, contacting the Zika virus isolate with different amounts of at least one candidate drug compound, contacting the protease substrate with the Zika virus isolate and the at least one candidate compound, quantifying the amount of peptide released by the at least one Zika virus protease, and selecting a drug compound as useful for the prevention and/or treatment of Zika virus infection when the concentration of the compound at which a 50% reduction in ZIKA protease activity can be measured is less than 50 µg/ml.

Also disclosed are methods for identifying compounds that are useful for the prevention and/or treatment of Zika virus infection where the method involves providing the crystal structure of a Zika virus non-structural protein, providing candidate drug compounds, building a protein model system, conducting molecular dynamics simulations to predict the stability of Zika virus nonstructural protein-compound complexes, selecting compounds that form stable complexes with Zika virus non-structural proteins, providing a Zika virus-susceptible cell line, providing a Zika virus isolate, contacting the Zika virus-susceptible cell line with the Zika virus isolate in the presence and absence of increasing concentrations of at least one selected compound, determining the cytopathic effect of the Zika virus isolate on the Zika virus-susceptible cell line, and selecting a compound as useful for the prevention and/or treatment of Zika virus infection when the concentration of the compound at which a 50% reduction in the cytopathic effect can be measured is less than 50 µg/ml.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 1 is a diagram showing the screening and validation strategies used to identify compounds useful for prevention and treatment of Zika virus infection.

FIG. 2A is a graph of fluorescence intensity versus protein concentration in the presence of different concentrations of novobiocin. FIG. 2B is a graph of normalized response versus the log of aprotinin concentration. FIG. 2C is a graph of normalized response versus the log of novobiocin concentration. Data are presented as mean values±standard error of the mean (error bars). $IC_{50}$, half maximal inhibitory concentration (concentration of the drug at which there was 50% reduction in protease activity).

FIG. 4A is a graph of log viral blood load versus concentration of novobiocin in Vero cells. FIG. 4B is a graph of log viral blood load versus concentration of novobiocin in Huh-7 cells. FIG. 4C is a graph of plaque reduction (%) versus concentration of novobiocin. All experiments were performed in triplicates and repeated twice for confirmation. * denotes P<0.05 and *** denotes P<0.0001 (compared to the DMSO control group by Student's t test). Data are presented as mean values±standard error of the mean (error bars).

FIG. 5A is a graph of log normalized viral load versus concentration of lopinavir-ritonavir in Vero cells. FIG. 5B is a graph of log normalized viral load versus concentration of lopinavir-ritonavir in Huh-7 cells. All experiments were performed in triplicates. * denotes P<0.05 and *** denotes P<0.0001 (compared to the DMSO control group by Student's t test). Data are presented as mean values±standard error of the mean (error bars).

FIG. 6A is a graph of weight change versus days post-inoculation of Zika virus. FIG. 6B is a graph of clinical score versus days post-inoculation of Zika virus. FIG. 6C is a graph of survival (%) versus days post-inoculation of Zika virus.

DETAILED DESCRIPTION OF THE INVENTION

Figure 2A:
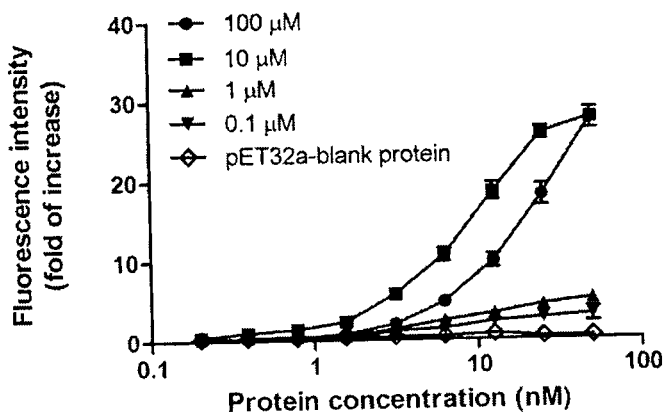
FIGS. 2A-2C are graphs showing the inhibition of protease activity of ZIKV-NS2B-NS3 by novobiocin.

The disclosed method and compositions may be understood more readily by reference to the following detailed description of particular embodiments and the Example included therein and to the Figures and their previous and following description.

I. Compounds and Compositions

Disclosed are compositions for preventing and/or treating Zika virus (ZIKV) infection. It was discovered that a useful approach to discover anti-ZIKV treatments is by repurposing clinically approved drugs that fortuitously inhibit the key enzymes of ZIKV, including, for example, the ZIKV protease, helicase, and/or polymerase. Based on this discovery, drug compounds have been identified by in silico virtual screening, which have high affinity towards the ZIKV protease ZIKV-NS2B-NS3 and are capable of inhibiting ZIKV-NS2B-NS3 activity in vitro and in vivo.

In some forms, the composition inhibits Zika virus helicase. In some forms, the composition inhibits Zika virus polymerase. In specific forms, the composition inhibits Zika virus protease.

A. Novobiocin

Novobiocin, also known as albamycin or cathomycin, is an antibiotic that is produced by the actinomycete *Streptomyces niveus*. It is active against *Staphylococcus epidermidis*, but may also be used as an antistaphylococcal agent used in the treatment of MRSA. Novobiocin is an inhibitor of bacterial DNA gyrase and works by targeting the GyrB subunit of the enzyme involved in energy transduction. It acts as a competitive inhibitor of the ATPase reaction catalysed by GyrB. The GyrA subunit is involved in the DNA nicking and ligation activity.

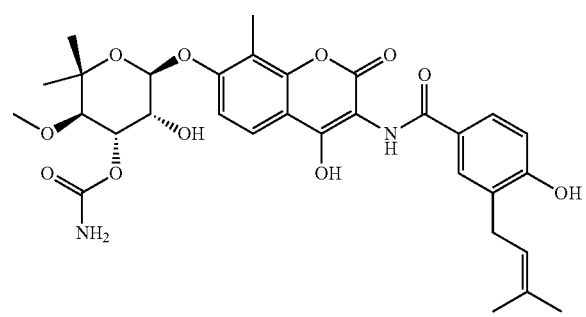

Novobiocin

B. Lopinavir-ritonavir

Lopinavir-ritonavir is a fixed dose combination medication for the treatment and prevention of HIV/AIDS. Both lopinavir and ritonavir are HIV protease inhibitors. The drug is generally recommended for use with other antiretroviral drugs. It may be used for prevention after a needlestick injury or other potential exposure. It is taken by mouth as a tablet or solution. It is commonly used in pregnancy and it appears to be safe. Ritonavir functions by slowing down the breakdown of lopinavir.

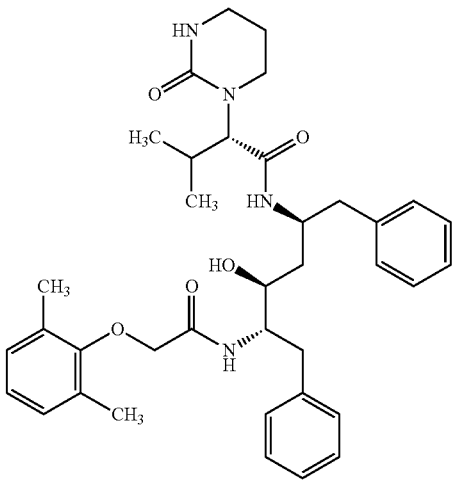

Lopinavir

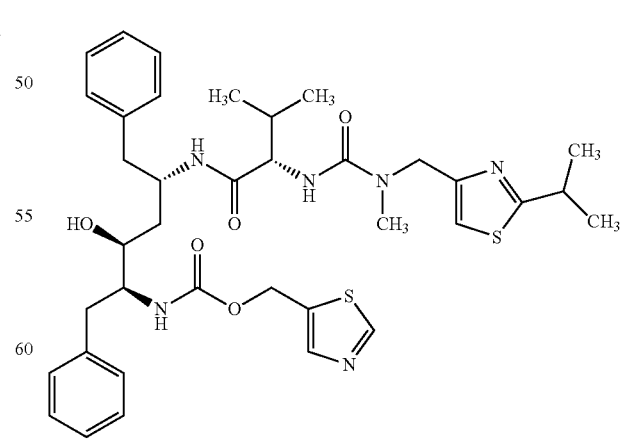

Ritonavir

C. Rifampicin

Rifampicin, also known as rifampin, is an antibiotic made by the soil bacterium *Amycolatopsis rifamycinica*, and is used to treat several types of bacterial infections, such as tuberculosis, leprosy, and Legionnaire's disease. It is almost always used along with other antibiotics, except when given to prevent *Haemophilus influenzae* type b and meningococcal disease in people who have been exposed to those bacteria. Rifampicin may be given either by mouth or intravenously, and is part of the recommended treatment of active tuberculosis during pregnancy. This drug works by inhibiting bacterial DNA-dependent RNA polymerase, thus stopping the production of RNA by bacteria. It has also been shown to be effective against vaccinia virus.

D. Desmopressin Acetate

Desmopressin is a synthetic version of vasopressin, the hormone that reduces urine production. This drug is usually prescribed in the form of desmopressin acetate, and is commonly used to treat diabetes insipidus, bedwetting, hemophilia A, von Willebrand disease, and high blood urea levels. It may be administered in the nose, by injection into a vein, by mouth, or under the tongue. Use of this drug appears to be safe during pregnancy. Desmopressin is an antidiuretic, and thus works by limiting the amount of water that is eliminated in the urine. It works at the level of the renal collecting duct by binding to V2 receptors, which signal for the translocation of aquaporin channels via cytosolic vesicles to the apical membrane of the collecting duct. The presence of these aquaporin channels in the distal nephron causes increasing water reabsorption from the urine, which becomes passively re-distributed from the nephron to systemic circulation by way of basolateral membrane channels. Desmopressin also stimulates release of von Willebrand factor from endothelial cells by acting on the V2 receptor. As illustrated in the Examples, desmopressin acetate is also capable of inhibiting ZIKV-NS2B-NS3 activity in vitro and in vivo.

Desmopressin

Rifampicin

E. Octreotide Acetate

Octreotide is an octapeptide that mimics natural somatostatin pharmacologically, though it is a more potent inhibitor of growth hormone, glucagon, and insulin than the natural hormone. Octreotide is used for the treatment of growth hormone producing tumors (acromegaly and gigantism), pituitary tumors that secrete thyroid stimulating hormone (thyrotropinoma), diarrhea and flushing episodes associated with carcinoid syndrome, and diarrhea in people with vasoactive intestinal peptide-secreting tumors. Octreotide is also often given as an infusion for management of acute haemorrhage from esophageal varices in liver cirrhosis. It is also used in nuclear medicine imaging by labelling with indium-111 (Octreoscan) to noninvasively image neuroendocrine and other tumors expressing somatostatin receptors. Octreotide also helps in management of the fistula by reducing GI secretions and inhibiting GI motility, thus controlling and reducing its output. As illustrated in the Examples, desmopressin acetate is also capable of inhibiting ZIKV-NS2B-NS3 activity in vitro and in vivo.

Octreotide

The pharmaceutical compositions described herein can include, but are not limited to, carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

Disclosed are validated ZIKV-NS2B-NS3 protease inhibitors to inhibit ZIKV replication in vitro. In some forms of the methods, ZIKV-NS2B-NS3 protease inhibitors novobiocin and lopinavir-ritonavir can be used to inhibit ZIKV replication in vitro and in vivo. It was discovered that treatment with novobiocin significantly improved the clinical outcome of mice in an animal model of disseminated ZIKV infection.

In some forms, the composition described herein contains an effective amount of novobiocin, lopinavir-ritonavir, rifampicin, desmopressin acetate, octreotide acetate, or a combination thereof. In some forms, the composition contains an effective amount of novobiocin, lopinavir-ritonavir, or combinations thereof. In some forms, the composition contains an effective amount of novobiocin.

However, as is generally understood by those of skill in the art, compositions may contain additional compounds and are thus not limited to the compounds described herein. In some forms, the compositions contain at least one compound of the compounds listed in Table 2.

As used herein, the term "activity" refers to a biological activity.

As used herein, the term "pharmacological activity" refers to the inherent physical properties of a peptide or polypeptide. These properties include but are not limited to half-life, solubility, and stability and other pharmacokinetic properties.

II. Methods of Screening and Identifying Compounds

The disclosed methods of identifying compounds useful for preventing or treating Zika virus infection can be performed in any suitable manner. Generally, the first goal of the identification methods if to identify compounds having one or more desired characteristics. This can be followed by screening or identification of those compound hit for the presence of one or more other desired characteristics. Screening and identification can be either for the presence of a characteristic or a particular level of the characteristic, or a level of the characteristic over a threshold level. The desired characteristics can be any characteristics that are relevant to the ultimate goal. It has been discovered that useful characteristics for identifying compound that can be useful for preventing or treating Zika virus infection include (a) that the compound is predicted to form a stable complex with a Zika virus non-structural protein (such as Zika virus protease, helicase, or polymerase) using molecular dynamics simulations, (b) that the compound is predicted to form a complex with a Zika virus non-structural protein (such as Zika virus protease, helicase, or polymerase) that is stable to or above a threshold level of stability using molecular dynamics simulations, (c) that the compound inhibits a Zika virus non-structural protein (such as Zika virus protease, helicase, or polymerase), (d) that the compound inhibits a Zika virus non-structural protein (such as Zika virus protease, helicase, or polymerase) to or above a threshold level of inhibition, (e) that the compound reduces the level of a cytopathic effect of a Zika virus isolate on a Zika virus-susceptible cell line, (f) that the compound reduces the level of a cytopathic effect of a Zika virus isolate on a Zika virus-susceptible cell line to or above a threshold level cytopathic effect, (g) that the compound has no or low toxicity to subjects to be treated with the compound, (h) that the compound has toxicity to subjects to be treated with the compound below a threshold of toxicity, (i) that the compound has no or low toxicity to a particular cell or tissue, and (j) that the compound has toxicity to a particular cell or tissue below a threshold of toxicity.

A stable complex can be assessed in terms of, for example, the energy state of the interaction of the compound and the binding partner. Other measures of stability know to those of skill in the art can also be used. A useful threshold level of stability can be the dynamic behavior of the complex, which can be assessed by, for example, performing molecular dynamic simulations. For example, the complex can be stable (a) for at least, (b) for, or (c) greater than 10 ns, 15 ns, 20 ns, 25 ns, 30 ns, 35 ns, 40 ns, 45 ns, 50 ns, 55 ns, 60 ns, 65 ns, 70 ns, 75 ns, 80 ns, 85 ns, 90 ns, 95 ns, 100 ns, 110 ns, 120 ns, 130 ns 140 ns 150 ns, 160 ns, 170 ns, 180 ns, 190 ns, or 200 ns. The trajectories produced in the disclosed studies reveal that the complex is fairly stable during an event of 50 ns. Inhibition can be assessed in terms of, for example, a reduction in the activity of the inhibited protein (such as reduced protease activity for a protease). The activity measured for assessing inhibition can be any activity of the protein but generally can be the main activity of the protein. The activity can be measured using any suitable assay technique, such as by using a special, model, or indicator substrate for the activity. Any suitable cytopathic effect of Zika virus on a Zika virus-susceptible cell line can be used to assess a reduction in a cytopathic effect. For example, the cytopathic effect assessed can be cellular growth restriction, cell cycle dysregulation, induction of cellular hypertrophy, induction of stress granules, increase in ER proliferation, or apoptosis. Such cytopathic effects can be assessed using, for example, the assay described in the examples (also described in Chan et al. (2017a)). Cytopathic effect can also be assessed using virus yield reduction or plaque reduction. Virus yield reduction and plaque reduction can be assessed using, for example, the assays described in the examples (also described in Chan et al. (2017a)). A useful Zika virus isolate can be, for example, Puerto Rico strain PRVABC59. Useful Zika virus-susceptible cell lines include, for example, Vero cells and Huh-7 cells.

Toxicity of compounds on cells, tissues, and organisms can be assessed using any of the numerous techniques known for such purposes. Toxicity can be assessed by, for example, the killing effect of a compound, the development of an injury or pathological effect, or some other detrimental effect on the cell, tissue, or organism. For example, toxicity of a compound can be assessed by determining cytotoxicity of the compound on a suitable cell or cell line, such as Vero cells or Huh-7 cells. As a measure of toxicity, the 50% effective cytotoxic concentration of the compound can be measured, for example. Cytotoxicity can be assessed using, for example, the assay described in the examples (also described in Chan et al. (2017a)).

Disclosed are methods to identify compounds useful for prevent or treat Zika virus infection. For example, disclosed are methods for identifying a compound that inhibits Zika virus protease where the method involves (a) bringing into contact, in a first test chamber, a protease substrate, a test compound, and a Zika virus isolate comprising at least one Zika virus protease, and (b) measuring the amount of the protease substrate that is cleaved in the first test chamber. In some forms, the test compound can be identified as a compound that inhibits Zika virus protease if the measured amount of cleaved protease substrate in the first test chamber is less than the amount of cleaved protease substrate measured in a control test chamber having no test compound.

In some forms, steps (a) and (b) can be performed in one or more additional test chambers, each having an amount of the test compound different from the amount of test compound in the first test chamber. In some forms, the test compound can be identified as a compound that inhibits Zika virus protease if the measured amount of cleaved protease substrate in one of the test chambers having less than 50 µg/ml of the test compound is at least 50% less than the amount of cleaved protease substrate measured in the control test chamber.

In some forms, the first test chamber can have less than 50 µg/ml of the test compound. In some forms, the test compound can be identified as a compound that inhibits Zika virus protease if the measured amount of cleaved protease substrate in the first test chamber is at least 50% less than the amount of cleaved protease substrate measured in the control test chamber.

Also disclosed are methods for the systematic in silico, in vitro, and in vivo screening of treatments for ZIKV infection and the development of novel anti-ZIKV agents. An in silico structure-based virtual screening of a large chemical library consisting of 8227 drug compounds to identify potential ZIKV-NS2B-NS3 protease inhibitors was performed as illustrated in the Examples. The ZIKV-NS2B-NS3 protease crystal structure was utilized as inputs to the program (Lei et al., Science 353, 503-505 (2016)) and the top 100 primary hit compounds were ranked by their predicted binding affinities to the ZIKV-NS2B-NS3 protease (Table 2).

In some forms, the test compound can be a compound identified as a compound that is predicted to form a stable complex with a Zika virus protease using molecular dynamics simulations. In some forms, the molecular dynamics simulations can use a protein model system built using the crystal structure of a Zika virus protease and the structure of candidate compounds. Molecular dynamics simulations, and platforms for such simulations, are known and can be used for the disclosed methods. Generally, any molecular dynamics simulation that assesses binding interactions of two or more components can be used. The molecular dynamics simulation used in the examples, Lead Finder (BioMolTech), can be used, for example. Protein model system refers to the structural information for a protein present and used in a modeling system, such as a molecular dynamics simulation.

Also disclosed are methods for identifying compounds that are useful for the prevention and/or treatment of Zika virus infection where the method involves providing a protease substrate, providing candidate drug compounds, providing a Zika virus isolate comprising at least one Zika virus protease, contacting the Zika virus isolate with different amounts of at least one candidate drug compound, contacting the protease substrate with the Zika virus isolate and the at least one candidate compound, quantifying the amount of peptide released by the at least one Zika virus protease, and selecting a drug compound as useful for the prevention and/or treatment of Zika virus infection when the concentration of the compound at which a 50% reduction in ZIKA protease activity can be measured is less than 50 µg/ml.

Exemplary candidate drug compounds include, but are not necessarily limited to the drug compounds listed in Table 2.

In specific forms, methods of screening are aimed at compounds that inhibit Zika virus protease. Such methods may involve (a) bringing into contact, in a first test chamber, a protease substrate, a test compound, and a Zika virus isolate comprising at least one Zika virus protease; and (b) measuring the amount of the protease substrate that is cleaved in the first test chamber, where the test compound is identified as a compound that inhibits Zika virus protease if the measured amount of cleaved protease substrate in the first test chamber is less than the amount of cleaved protease substrate measured in a control test chamber having no test compound.

In some forms, steps (a) and (b) are performed in one or more additional test chambers, each having an amount of the test compound different from the amount of test compound in the first test chamber, where the test compound is identified as a compound that inhibits Zika virus protease if the measured amount of cleaved protease substrate in one of the test chambers having less than 50 µg/ml of the test compound is at least 50% less than the amount of cleaved protease substrate measured in the control test chamber.

In some forms, the first test chamber has less than 50 µg/ml of the test compound, wherein the test compound is identified as a compound that inhibits Zika virus protease if the measured amount of cleaved protease substrate in the first test chamber is at least 50% less than the amount of cleaved protease substrate measured in the control test chamber.

In some forms, the test compound is a compound identified as a compound that is predicted to form a stable complex with a Zika virus protease using molecular dynamics simulations.

In some forms, the molecular dynamics simulations use a protein model system built using the crystal structure of a Zika virus protease and the structure of candidate compounds.

Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

Also disclosed are methods for identifying a compound that inhibits Zika virus infection where the method involves (a) bringing into contact, in a first test chamber, a Zika virus-susceptible cell line, a test compound, and a Zika virus isolate, and (b) measuring the level of a cytopathic effect of the Zika virus isolate on the Zika virus-susceptible cell line in the first test chamber. In some forms, the test compound can be identified as a compound that inhibits Zika virus infection if the measured level of the cytopathic effect in the first test chamber is less than the level of the cytopathic effect measured in a control test chamber having no test compound.

In some forms, steps (a) and (b) can be performed in one or more additional test chambers, each having an amount of the test compound different from the amount of test compound in the first test chamber. In some forms, the test compound can be identified as a compound that inhibits Zika virus infection if the measured level of the cytopathic effect in one of the test chambers having less than 50 µg/ml of the test compound is at least 50% less than the level of the cytopathic effect measured in the control test chamber.

In some forms, the first test chamber can have less than 50 µg/ml of the test compound. In some forms, the test compound can be identified as a compound that inhibits Zika virus infection if the measured level of the cytopathic effect in the first test chamber is at least 50% less than the level of the cytopathic effect measured in the control test chamber.

In some forms, the test compound can be a compound identified as a compound that is predicted to form a stable complex with a Zika virus non-structural protein using molecular dynamics simulations. In some forms, the molecular dynamics simulations can use a protein model system built using the crystal structure of a Zika virus non-structural protein and the structure of candidate compounds.

Also disclosed are methods for identifying compounds that are useful for the prevention and/or treatment of Zika virus infection where the method involves providing the crystal structure of a Zika virus non-structural protein, providing candidate drug compounds, building a protein model system, conducting molecular dynamics simulations to predict the stability of Zika virus nonstructural protein-compound complexes, selecting compounds that form stable complexes with Zika virus non-structural proteins, providing a Zika virus-susceptible cell line, providing a Zika virus isolate, contacting the Zika virus-susceptible cell line with the Zika virus isolate in the presence and absence of increasing concentrations of at least one selected compound, determining the cytopathic effect of the Zika virus isolate on the Zika virus-susceptible cell line, and selecting a compound as useful for the prevention and/or treatment of Zika virus infection when the concentration of the compound at which a 50% reduction in the cytopathic effect can be measured is less than 50 µg/ml.

In specific forms, methods of screening are aimed at compounds that inhibit Zika virus infection. Such methods may involve (a) bringing into contact, in a first test chamber, a Zika virus-susceptible cell line, a test compound, and a Zika virus isolate; and (b) measuring the level of a cytopathic effect of the Zika virus isolate on the Zika virus-susceptible cell line in the first test chamber, where the test compound is identified as a compound that inhibits Zika virus infection if the measured level of the cytopathic effect in the first test chamber is less than the level of the cytopathic effect measured in a control test chamber having no test compound.

In some forms, steps (a) and (b) are performed in one or more additional test chambers, each having an amount of the test compound different from the amount of the test compound in the first test chamber, where the test compound is identified as a compound that inhibits Zika virus infection if the measured level of the cytopathic effect in one of the test chambers having less than 50 µg/ml of the test compound is at least 50% less than the level of the cytopathic effect measured in the control test chamber.

In some forms, the first test chamber has less than 50 µg/ml of the test compound, where the test compound is identified as a compound that inhibits Zika virus infection if the measured level of the cytopathic effect in the first test chamber is at least 50% less than the level of the cytopathic effect measured in the control test chamber.

In some forms, the test compound is a compound identified as a compound that is predicted to form a stable complex with a Zika virus non-structural protein using molecular dynamics simulations.

In some forms, the molecular dynamics simulations use a protein model system built using the crystal structure of a Zika virus non-structural protein and the structure of candidate compounds.

As those of skill in the art know, additional methods of screening compounds are envisioned, and are hence not limited to the methods described herein.

Test chambers refer to tubes, wells, containers, spots on a substrate, etc. in which components of different assays or samples can be held or placed. Separate test chambers refer different test chambers in which mixtures, reactions, or assays can be placed or performed without interfering with or combining with other mixtures, reactions, or assays in other test chambers. Examples of components comprising or including test chambers are well plates, tubes, containers, surfaces, slides, etc.

The term "bringing into contact" as used herein refers to any form, mode, or technique of adding, mixing, combining, etc. a component (such as compound or molecule) to another component. Bringing into contact also encompasses taking an action that will result in a component coming into contact with another component.

The term "hit" refers to a test compound that shows desired properties in an assay. The term "test compound" refers to a chemical to be tested by one or more screening method(s) as a putative modulator. A test compound can be any chemical, such as an inorganic chemical, an organic chemical, a protein, a peptide, a carbohydrate, a lipid, or a combination thereof. Usually, various predetermined concentrations of test compounds are used for screening, such as 0.01 micromolar, 1 micromolar and 10 micromolar. Test compound controls can include the measurement of a signal in the absence of the test compound or comparison to a compound known to modulate the target. As used herein, the term "candidate compound" refers to a chemical, the structure of which is to be tested by one or more screening method(s) as forming a stable complex with a target structure using molecular dynamics simulations.

The term "modulate" as used herein refers to the ability of a compound to change an activity in some measurable way as compared to an appropriate control. As a result of the presence of compounds in the assays, activities can increase or decrease as compared to controls in the absence of these compounds. Preferably, an increase in activity is at least 25%, more preferably at least 50%, most preferably at least 100% compared to the level of activity in the absence of the compound. Similarly, a decrease in activity is preferably at least 25%, more preferably at least 50%, most preferably at least 100% compared to the level of activity in the absence of the compound. A compound that increases a known activity is an "agonist." One that decreases, or prevents, a known activity is an "antagonist."

The term "inhibit" means to reduce or decrease in activity or expression. This can be a complete inhibition of activity or expression, or a partial inhibition. Inhibition can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

III. Methods of Using Compositions

Also disclosed are methods for preventing and/or treating Zika virus infection. In some forms, the methods involve administering to a subject suffering from, or being at risk of developing, a Zika virus infection an effective amount of a composition comprising an effective amount of a compound that binds to a Zika virus non-structural protein. In some forms, the methods involve administering at least one compound of the compounds of Table 2.

The term "preventing" as used herein refers to administering a compound prior to the onset of clinical symptoms of a disease or conditions so as to prevent a physical manifestation of aberrations associated with the disease or condition. In the context of Zika virus infection, the term "preventing" refers to administering a compound prior to the onset of clinical symptoms of Zika virus infection so as to prevent a physical manifestation of aberrations associated with Zika virus infection.

The terms "treatment" and "treating" as used herein refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount. In the context of a subject suffering from Zika virus infection, the terms "treatment" and "treating" refer to the medical management of a subject with the intent to cure, ameliorate, or stabilize Zika virus infection. In the context of a subject at risk of developing Zika virus infection, the terms "treatment" and "treating" refer to the medical management of a subject with the intent to prevent Zika virus infection.

A. Subjects

In some forms, the methods involve administering to a subject suffering from, or being at risk of developing, a Zika virus infection. A subject is generally considered to be suffering from Zika virus infection if the subject has been diagnosed with Zika virus infection and/or suffers from any symptoms associated with Zika virus infection, such as, including, but not limited to, fever, rash, headache, joint pain, conjunctivitis, muscle pain, severe neurological complications such as Guillain-Barré syndrome, meningoencephalitis, and myelitis, thrombocytopenia and disseminated intravascular coagulation with hemorrhagic complications, hepatic dysfunction, acute respiratory distress syndrome, shock, and multi-organ dysfunction syndrome. A subject is generally considered to be at risk of developing a Zika virus infection if the subject has traveled to an area with high incidence of Zika virus, if the subject has been exposed to mosquito bites, if the subject has had unprotected sex with a person infected with Zika virus, if the subject had a blood transfusion with contaminated blood, or if the subject was exposed to Zika virus in a laboratory or healthcare setting.

As used herein, "subject" includes, but is not limited to, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects. In one aspect, the compounds described herein can be administered to a subject comprising a human or an animal including, but not limited to, a mouse, dog, cat, horse, bovine or ovine and the like, that is in need of alleviation or amelioration from a recognized medical condition.

The term "monitoring" as used herein refers to any method in the art by which an activity can be measured.

The term "in need of treatment" as used herein refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that include the knowledge that the subject is ill, or will be ill, as the result of a condition that is treatable by the disclosed compounds.

The disclosed methods include the determination, identification, indication, correlation, diagnosis, prognosis, etc. (which can be referred to collectively as "identifications") of subjects, diseases, conditions, states, etc. based on measurements, detections, comparisons, analyses, assays, screenings, etc. For example, a subject can be determined to be, or identified as, at risk for Zika virus infection, a subject can be diagnosed, determined, or identified to be suffering from Zika virus infection, a compound can be determined to be, or identified as, a compound that inhibits Zika virus protease, a compound can be determined to be, or identified as, a compound that inhibits Zika virus infection, etc. The disclosed methods can include, for example, the identification of subjects at risk of being infected with Zika virus, or subjects having been diagnosed with Zika virus infection. Such subjects include healthy, immune competent, or immune compromised adults, elderly adults, children, and infants. In some forms the subjects are men. In some forms, the subjects are women. In specific forms, the subjects are pregnant women. Such identifications are useful for many reasons. For example, and in particular, such identifications allow specific actions to be taken based on, and relevant to, the particular identification made. For example, diagnosis of a particular disease or condition in particular subjects (and the lack of diagnosis of that disease or condition in other subjects) has the very useful effect of identifying subjects that would benefit from treatment, actions, behaviors, etc. based on the diagnosis. For example, treatment for a particular disease or condition in subjects identified is significantly different from treatment of all subjects without making such an identification (or without regard to the identification). Subjects needing or that could benefit from the treatment will receive it and subjects that do not need or would not benefit from the treatment will not receive it.

Accordingly, also disclosed herein are methods comprising taking particular actions following and based on the disclosed identifications. For example, disclosed are methods comprising creating a record of an identification (in physical—such as paper, electronic, or other—form, for example). Thus, for example, creating a record of an identification based on the disclosed methods differs physically and tangibly from merely performing a measurement, detection, comparison, analysis, assay, screen, etc. Such a record is particularly substantial and significant in that it allows the identification to be fixed in a tangible form that can be, for example, communicated to others (such as those who could treat, monitor, follow-up, advise, etc. the subject based on the identification); retained for later use or review; used as data to assess sets of subjects, treatment efficacy, accuracy of identifications based on different measurements, detections, comparisons, analyses, assays, screenings, etc., and the like. For example, such uses of records of identifications can be made, for example, by the same individual or entity as, by a different individual or entity than, or a combination of the same individual or entity as and a different individual or entity than, the individual or entity that made the record of the identification. The disclosed methods of creating a record can be combined with any one or more other methods disclosed herein, and in particular, with any one or more steps of the disclosed methods of identification.

As another example, disclosed are methods comprising making one or more further identifications based on one or more other identifications. For example, particular treatments, monitorings, follow-ups, advice, etc. can be identified based on the other identification. For example, identification of a subject as having a disease or condition with a high level of a particular component or characteristic can be further identified as a subject that could or should be treated with a therapy based on or directed to the high level component or characteristic. A record of such further identifications can be created (as described above, for example) and can be used in any suitable way. Such further identifications can be based, for example, directly on the other identifications, a record of such other identifications, or a combination. Such further identifications can be made, for example, by the same individual or entity as, by a different individual or entity than, or a combination of the same individual or entity as and a different individual or entity than, the individual or entity that made the other identifications. The disclosed methods of making a further identification can be combined with any one or more other methods disclosed herein, and in particular, with any one or more steps of the disclosed methods of identification.

As another example, disclosed are methods comprising treating, monitoring, following-up with, advising, etc. a subject identified in any of the disclosed methods. Also disclosed are methods comprising treating, monitoring, following-up with, advising, etc. a subject for which a record of an identification from any of the disclosed methods has been made. For example, particular treatments, monitorings, follow-ups, advice, etc. can be used based on an identification and/or based on a record of an identification. For example, a subject identified as having a disease or condition with a high level of a particular component or characteristic (and/or a subject for which a record has been made of such an identification) can be treated with a therapy based on or directed to the high level component or characteristic. Such treatments, monitorings, follow-ups, advice, etc. can be based, for example, directly on identifications, a record of such identifications, or a combination. Such treatments, monitorings, follow-ups, advice, etc. can be performed, for example, by the same individual or entity as, by a different individual or entity than, or a combination of the same individual or entity as and a different individual or entity than, the individual or entity that made the identifications and/or record of the identifications. The disclosed methods of treating, monitoring, following-up with, advising, etc. can be combined with any one or more other methods disclosed herein, and in particular, with any one or more steps of the disclosed methods of identification.

B. Forms and Modes of Administration

The term "providing" as used herein refers to any means of adding a compound or molecule to something known in the art. Examples of providing can include the use of pipettes, pipettemen, syringes, needles, tubing, guns, etc. This can be manual or automated. It can include transfection by any mean or any other means of providing nucleic acids to dishes, cells, tissue, cell-free systems and can be in vitro or in vivo.

The compounds and pharmaceutical compositions described herein can be administered to the subject in a number of ways depending on whether local or systemic treatment is desired, and on the area to be treated. Thus, for example, a compound or pharmaceutical composition described herein can be administered as an ophthalmic solution and/or ointment to the surface of the eye. Moreover, a compound or pharmaceutical composition can be administered to a subject vaginally, rectally, intranasally, orally, by inhalation, or parenterally, for example, by intradermal, subcutaneous, intramuscular, intraperitoneal, intrarectal, intraarterial, intralymphatic, intravenous, intrathecal and intratracheal routes. Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

Preparations for parenteral administration include sterile aqueous or non-aqueous solutions, suspensions, and emulsions which can also contain buffers, diluents and other suitable additives. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Compositions for oral administration can include powders or granules, suspensions or solutions in water or non-aqueous media, capsules, sachets, or tablets. Thickeners, flavorings, diluents, emulsifiers, dispersing aids or binders can be desirable.

C. Dosage

In some forms, the methods involve administering to a subject suffering from, or being at risk of developing, a Zika virus infection an effective amount of a composition comprising an effective amount of a compound that inhibits a Zika virus non-structural protein activity. The amount of compound that inhibits Zika virus non-structural protein activity by at least 50% can be an amount from a low of about 0.1 µg/ml, about 0.2 µg/ml, or about 0.5 µg/ml, to a high of about 100 µg/ml, about 200 µg/ml, or about 500 µg/ml. For example, the amount of compound that inhibits the activity of a Zika virus non-structural protein can be from about 0.1 µg/ml to about 100 µg/ml, from about 0.2 µg/ml to about 200 µg/ml, from about 0.5 µg/ml to about 500 µg/ml, from about 0.1 µg/ml to about 10 µg/ml, from about 0.1 µg/ml to about 20 µg/ml, from about 0.1 µg/ml to about 50 µg/ml, from about 0.5 µg/ml to about 20 µg/ml, from about 0.5 µg/ml to about 50, from about 0.5 µg/ml to about 100 µg/ml, from about 0.5 to about 200 µg/ml, from about 0.5 µg/ml to about 500 µg/ml, from about 15 µg/ml to about 25 µg/ml, from about 15 µg/ml to about 50, from about 18 µg/ml to about 30 µg/ml, from about 18 µg/ml to about 50 µg/ml.

In some forms, the dosage can be an amount to result in a concentration in one or more body fluids of a subject of from a low of about 0.1 µg/ml, about 0.2 µg/ml, or about 0.5 µg/ml, to a high of about 100 µg/ml, about 200 µg/ml, or about 500 µg/ml. For example, the dosage can be an amount to result in a concentration in one or more body fluids of a subject of from about 0.1 µg/ml to about 100 µg/ml, from about 0.2 µg/ml to about 200 µg/ml, from about 0.5 µg/ml to about 500 µg/ml, from about 0.1 µg/ml to about 10 µg/ml, from about 0.1 µg/ml to about 20 µg/ml, from about 0.1 µg/ml to about 50 µg/ml, from about 0.5 µg/ml to about 20 µg/ml, from about 0.5 µg/ml to about 50 µg/ml, from about 0.5 µg/ml to about 100 µg/ml, from about 0.5 to about 200 µg/ml, from about 0.5 µg/ml to about 500 µg/ml, from about 15 µg/ml to about 25 µg/ml, from about 15 µg/ml to about 50, from about 18 µg/ml to about 30 µg/ml, from about 18 µg/ml to about 50 µg/ml.

In some forms, the dosage can be an amount to result in a concentration in one or more body fluids of a subject of ranging from 0.1 µg/ml to 500 µg/ml. For example, the concentration can be (a) in the range of, (b) in the range of about, (c) from, or (d) from about any one of 0.1 µg/ml, 0.15 µg/ml, 0.2 µg/ml, 0.25 µg/ml, 0.3 µg/ml, 0.35 µg/ml, 0.4 µg/ml, 0.45 µg/ml, 0.5 µg/ml, 0.55 µg/ml, 0.6 µg/ml, 0.65 µg/ml, 0.7 µg/ml, 0.75 µg/ml, 0.8 µg/ml, 0.85 µg/ml, 0.9 µg/ml, 0.95 µg/ml, 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 12 µg/ml, 14 µg/ml, 15 µg/ml, 16 µg/ml, 18 µg/ml, 20 µg/ml, 25 µg/ml, 30 µg/ml, 35 µg/ml, 40 µg/ml, 45 µg/ml, 50 µg/ml, 55 µg/ml, 60 µg/ml, 65 µg/ml, 70 µg/ml, 75 µg/ml, 80 µg/ml, 85 µg/ml, 90 µg/ml, 95 µg/ml, 100 µg/ml, 110 µg/ml, 120 µg/ml, 125 µg/ml, 130 µg/ml, 140 µg/ml, 150 µg/ml, 160 µg/ml, 170 µg/ml, 175 µg/ml, 180 µg/ml, 190 µg/ml, 200 µg/ml, 220 µg/ml, 240 µg/ml, 250 µg/ml, 260 µg/ml, 280 µg/ml, 300 µg/ml, 320 µg/ml, 340 µg/ml, 350 µg/ml, 360 µg/ml, 380 µg/ml, 400 µg/ml, 420 µg/ml, 440 µg/ml, 450 µg/ml, 460 µg/ml, 480 µg/ml, or 500 µg/ml (a) to, (b) to about, (c) to, or (d) to about any one of 0.1 µg/ml, 0.15 µg/ml, 0.2 µg/ml, 0.25 µg/ml, 0.3 µg/ml, 0.35 µg/ml, 0.4 µg/ml, 0.45 µg/ml, 0.5 µg/ml, 0.55 µg/ml, 0.6 µg/ml, 0.65 µg/ml, 0.7 µg/ml, 0.75 µg/ml, 0.8 µg/ml, 0.85 µg/ml, 0.9 µg/ml, 0.95 µg/ml, 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 12 µg/ml, 14 µg/ml, 15 µg/ml, 16 µg/ml, 18 µg/ml, 20 µg/ml, 25 µg/ml, 30 µg/ml, 35 µg/ml, 40 µg/ml, 45 µg/ml, 50 µg/ml, 55 µg/ml, 60 µg/ml, 65 µg/ml, 70 µg/ml, 75 µg/ml, 80 µg/ml, 85 µg/ml, 90 µg/ml, 95 µg/ml, 100 µg/ml, 110 µg/ml, 120 µg/ml, 125 µg/ml, 130 µg/ml, 140 µg/ml, 150 µg/ml, 160 µg/ml, 170 µg/ml, 175 µg/ml, 180 µg/ml, 190 µg/ml, 200 µg/ml, 220 µg/ml, 240 µg/ml, 250 µg/ml, 260 µg/ml, 280 µg/ml, 300 µg/ml, 320 µg/ml, 340 µg/ml, 350 µg/ml, 360 µg/ml, 380 µg/ml, 400 µg/ml, 420 µg/ml, 440 µg/ml, 450 µg/ml, 460 µg/ml, 480 µg/ml, or 500 µg/ml, all ranges inclusive of the endpoints.

In some forms, the dosage of the compound can be an amount to result in a concentration in one or more body fluids of a subject (a) can be or (b) can be about 500 µg/ml, 480 µg/ml, 460 µg/ml, 450 µg/ml, 440 µg/ml, 420 µg/ml, 400 µg/ml, 380 µg/ml, 360 µg/ml, 350 µg/ml, 340 µg/ml, 320 µg/ml, 300 µg/ml, 280 µg/ml, 260 µg/ml, 250 µg/ml, 240 µg/ml, 220 µg/ml, 200 µg/ml, 190 µg/ml, 180 µg/ml, 175 µg/ml, 170 µg/ml, 160 µg/ml, 150 µg/ml, 140 µg/ml, 130 µg/ml, 125 µg/ml, 120 µg/ml, 110 µg/ml, 100 µg/ml, 95 µg/ml, 90 µg/ml, 85 µg/ml, 80 µg/ml, 75 µg/ml, 70 µg/ml, 65 µg/ml, 60 µg/ml, 55 µg/ml, 50 µg/ml, 45 µg/ml, 40 µg/ml, 35 µg/ml, 30 µg/ml, 25 µg/ml, 20 µg/ml, 18 µg/ml, 16 µg/ml, 15 µg/ml, 14 µg/ml, 12 µg/ml, 10 µg/ml, 9 µg/ml, 8 µg/ml, 7 µg/ml, 6 µg/ml, 5 µg/ml, 4 µg/ml, 3 µg/ml, 2 µg/ml, 1 µg/ml, 0.95 µg/ml, 0.9 µg/ml, 0.85 µg/ml, 0.8 µg/ml, 0.75 µg/ml, 0.7 µg/ml, 0.65 µg/ml, 0.6 µg/ml, 0.55 µg/ml, 0.5 µg/ml, 0.45 µg/ml, 0.4 µg/ml, 0.35 µg/ml, 0.3 µg/ml, 0.25 µg/ml, 0.2 µg/ml, 0.15 µg/ml, or 0.1 µg/ml.

In some forms, the concentration can range from 0.1 µg/ml to 10 µg/ml. In some forms, the concentration can range from 0.1 µg/ml to 5 µg/ml. In some forms, the concentration can range from 0.1 µg/ml to 1 µg/ml.

The terms "high," "higher," "increases," "elevates," or "elevation" refer to increases above basal levels, e.g., as compared to a control. The terms "low," "lower," "reduces," or "reduction" refer to decreases below basal levels, e.g., as compared to a control.

By the term "effective amount" of a compound as provided herein is meant a nontoxic but sufficient amount of the compound to provide the desired result. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation. In the context of compounds and compositions for prevention of Zika virus infection, the term "effective amount" of a compound as provided herein is meant a nontoxic but sufficient amount of the compound to prevent Zika virus infection. In the context of compounds and compositions for treatment of a subject suffering from Zika virus infection, the term "effective amount" of a compound as provided herein is meant a nontoxic but sufficient amount of the compound to treat Zika virus infection.

The dosages or amounts of the compounds described herein are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied.

The efficacy of administration of a particular dose of the compounds or compositions according to the methods described herein can be determined by evaluating the particular aspects of the medical history, signs, symptoms, and objective laboratory tests that are known to be useful in evaluating the status of a subject in need treatment of Zika virus infection or other diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: (1) a subject's physical condition is shown to be improved (e.g., a tumor has partially or fully regressed), (2) the progression of the disease or condition is shown to be stabilized, or slowed, or reversed, or (3) the need for other medications for treating the disease or condition is lessened or obviated, then a particular treatment regimen will be considered efficacious.

By "pharmaceutically acceptable" is meant a material that is not biologically or otherwise undesirable, i.e., the material can be administered to a subject along with the selected compound without causing any undesirable biological effects or interacting in a deleterious manner with any of the other components of the pharmaceutical composition in which it is contained.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

EXAMPLES

Materials and Methods

In Silico Structure-Based Virtual Screening of Chemical Library and Molecular Docking All compounds deposited in the DrugBank v5.0.1 were set up for docking simulations by using AmberTools (AMBER 2017, University of California, San Francisco) (Case et al., 2017). The crystal structure of the ZIKV NS2B-NS3 protease (Protein Data Bank (PDB) code 5LC0) was used to build up the protein model system (Lei et al., 2016). Molecular parameters were calculated by removing salts and neutralizing their protonation state, computing partial charges by MMFF94 force field, adding hydrogen atoms and minimizing energies (default parameters) (Halgren, 1995). The crystal structure of ZIKV NS2B-NS3 protease (Protein Data Bank (PDB) code 5LC0) was used to build up the protein model system (Lei et al., 2016). At an early stage, bond orders were assigned, hydrogens were added, and cap termini were included with the Protein Preparation Wizard module as implemented in Maestro (Schrödinger Release 2016-4: Maestro, Schrödinger, LLC, New York, USA) (Sastry et al., 2013). Protonation states of all side chains were subsequently defined using PROPKA3.1. Partial charges over all atoms were finally assigned within the AMBER99 force field scheme as implemented in AmberTools (AMBER 2017, University of California, San Francisco) (Case et al., 2017). Docking simulations were performed with Lead Finder software v1.1.16 (Stroganov et al., 2008). All docking parameters were set to default for the calculations. The best ranked docking score posed for every compound was retained for further analysis.

Molecular Dynamics Simulations

Molecular dynamics simulations were conducted to predict the stability of the novobiocin-ZIKV NS2B-NS3 complex. The calculations were performed with Desmond (Desmond Molecular Dynamics System, D. E. Shaw Research, and Maestro-Desmond Interoperability Tools, Schrödinger, LLC, New York, USA) in combination with the OPLS-2005 Force Field (Shivakumar et al., 2010).

Virus Strain and Titration

A clinical isolate of ZIKV (Puerto Rico strain PRV-ABC59) obtained from a patient in the recent South American epidemic was kindly provided by Brandy Russell and Barbara Johnson, Centers for Disease Control and Prevention, USA. The virus was cultured and titrated as we previously described with slight modifications (Chan et al., 2016b; Zhou et al., 2014). The virus was amplified by three additional passages in Vero cells (ATCC) in minimum essential medium (MEM) supplemented with 1% fetal bovine serum (FBS, Gibco™, Life Technologies Corporation, Massachusetts, USA) and 100 units/ml penicillin plus 100 µg/ml streptomycin to make working stocks of the virus ($4\times10^6$ 50% tissue culture infectious dose ($TCID_{50}$)/ml). For virus titration, aliquots of ZIKV were applied on confluent Vero cells in 96-well plates for the $TCID_{50}$ assay as was previously described with slight modifications (Chan et al., 2016b; Zhou et al., 2014). Briefly, serial 10-fold dilutions of ZIKV were inoculated in a Vero cell monolayer in quadruplicate and cultured in penicillin/streptomycin-supplemented MEM and 1% FBS. The plates were observed for CPE for 6 days. Viral titer was calculated using the Reed and Munch endpoint method. One $TCID_{50}$ was interpreted as the amount of virus that causes cytopathic effect in 50% of inoculated wells.

Cell Lines and Drug Compounds

Vero and Huh-7 cell lines were obtained from the American Type Culture Collection and JCRB cell bank of Okayama University, Japan, respectively, as was previously described (Chan et al., 2013a; Chan et al., 2016b). Aprotinin (Sigma-Aldrich, Missouri, USA), desmopressin acetate (Ferring Pharmaceuticals, Saint Prex, Switzerland), lopinavir-ritonavir (Abbott Laboratories, Illinois, USA), montelukast (Merck & Co., Inc., New Jersey, USA), novobiocin sodium (Sigma-Aldrich Chemie GmbH, Steinheim, Germany), octreotide acetate (Novartis, Basel, Switzerland), rifampicin (Gruppo Lepetit Srl, Milan, Italy), sirolimus (Pfizer, New York city, USA), and tacrolimus (Astellas Pharma, Tokyo, Japan) were used for the in vitro and/or in vivo studies.

Cell Viability Assay and CPE Inhibition Assay

The 50% effective cytotoxic concentration ($CC_{50}$) of the selected drugs in Vero and Huh-7 cells were determined by thiazolyl blue tetrazolium bromide (MTT) assay as we previously described with modifications (Chan et al., 2017a; Yuan et al., 2016). Briefly, Vero or Huh-7 cells ($4 \times 10^4$ cells/well) were incubated with different concentrations of individual drug for 24 h, followed by the addition of 10 µl/well of 5 mg/ml MTT substrate. The monolayers were incubated as above for 4 h (away from light). Finally, 100 µl of 10% sodium dodecyl sulfate (SDS) with 0.01M HCl was added and further incubated at 37° C. with 5% $CO_2$ overnight. The activity was read at $OD_{570}$ with reference wavelength at $OD_{640}$. To confirm the antiviral activity of novobiocin, the MTT-based CPE inhibition assay was also performed as previously described with slight modifications (Chan et al., 2017a). Briefly, the drug compounds were diluted with serum-free MEM and added to confluent Vero cells in 96-well culture plates ($4 \times 10^4$ cells/well) in triplicate for 2 h at 37° C. After incubation, the drug-containing media were removed, and ZIKV (multiplicity of infection, MOI=0.0002) was added together with fresh drug-compound media to each well. Following 1 h of adsorption at 37° C., the virus-compound mixture was removed and the cells were washed twice with MEM to remove unbound virus. Subsequently, media with antiviral compounds were added to the cells for further incubation for 6 days at 37° C. in a 5% $CO_2$ humidified environment. CPE was examined by inverted light microscopy (Chan et al., 2016b). Thereafter, MTT substrate and SDS-HCl were added sequentially as mentioned above. The half maximal inhibitory concentration ($IC_{50}$) and $CC_{50}$ were calculated using Sigma plot (SPSS) in an Excel add-in ED50V10.

Viral Load Reduction Assay

Viral load reduction assay and plaque reduction assay was performed for the evaluation of antiviral activity. Briefly, ZIKV-infected Vero cells (MOI=0.05) were treated with different concentrations of drugs or dimethyl sulfoxide (DMSO) control, cell culture supernatants (Vero and Huh-7) were collected at 48 hours post-infection, followed by total nucleic acid extraction and quantitative reverse transcription-PCR (qRT-PCR) as previously described with modifications (Chan et al., 2013; Chan et al., 2016b; Chan et al., 2017a). The $IC_{50}$ was calculated using Sigma plot (SPSS) in an Excel add-in ED50V10. The viral load reduction assay experiments were performed in triplicate and repeated twice for confirmation.

Plaque Reduction Assay

Plaque reduction assay was performed as we previously described with slight modifications (Chan et al., 2017a). Briefly, Vero cells were seeded at $2 \times 10^5$ cells/well in 24-well tissue culture plates on the day before carrying out the assay. After 24 h of incubation, 20-40 plaque-forming units (PFU) of ZIKV were added to the cell monolayer with or without the addition of drug compounds and the plates were further incubated for 1 h at 37° C. in 5% $CO_2$ before removal of unbound viral particles by aspiration of the media and washing once with MEM. Monolayers were then overlaid with media containing 1% low melting agarose (Cambrex Corporation, New Jersey, USA) in MEM and appropriate concentrations of drug compounds, inverted and incubated as above for another 96 h. The wells were then fixed with 10% formaldehyde (BDH, Merck, Darmstadt, Germany) overnight. After removal of the agarose plugs, the monolayers were stained with 0.7% crystal violet (BDH, Merck) and the plaques were counted. The percentage of plaque inhibition relative to the control (i.e. without the addition of compound) wells were determined for each drug compound concentration. The $IC_{50}$ was calculated using Sigma plot (SPSS) in an Excel add-in ED50V10. The plaque reduction assay experiments were performed in triplicate and repeated twice for confirmation.

Time-of-Drug-Addition Assay

Time-of-drug-addition assay was performed for novobiocin to determine which phase(s) of virus cycle the drug interfered with (Chan et al., 2017a; Kato et al., 2016). Briefly, Vero cells were seeded in 24-well plates ($2 \times 10^5$ cells/well). The cells were inoculated with ZIKV (MOI=2) and then incubated for 1 h for virus internalization. The viral inoculum was then removed and the cells were washed twice with PBS. At 0, 3, 6, 9, 12, and 14 hours post-infection, 100 µg/ml novobiocin was added to the infected cells, followed by incubation at 37° C. in 5% $CO_2$ until 18 hours post-infection. For the time point of "−1 to 0 hpi," 100 µg/ml novobiocin was added at 1 h before infection and removed at 0 hpi, which was followed by ZIKV inoculation and incubation of the cells until 18 hpi. For the time point "0-1 hpi," 100 µg/ml of novobiocin was added together with ZIKV inoculation at 0 hpi, followed by drug removal at 1 hpi and incubation of the cells until 18 hpi. At 18 hpi, the cell culture supernatant of each time point experiment was collected for viral load measurement using qRT-PCR. Dimethyl sulfoxide (0.5%, 0 µg/ml novobiocin) was included as a negative control. The experiments were performed in triplicate and repeated twice for confirmation.

Protein Production and Purification

The recombinant ZIKV NS2B-NS3 protease was produced as previously described with some modifications (Lei et al., 2016). Briefly, coding regions of the ZIKV-NS2B (residues 49-95) and ZIKV-NS3 (residues 1-170) genes were fused and cloned into the pET-28b(+) expression vector (Novagen, Merck & Co., New Jersey, USA). The plasmid was transformed into *Escherichia coli* strain BL21

(DE3) and overexpressed in 2×YT medium. When the $OD_{600}$ of the culture reached 0.8, overexpression of the ZIKV NS2B-NS3 protease gene was induced for overnight by addition of 0.5 mM IPTG at 20° C. The ZIKV NS2B-NS3 protease was purified by His-tag affinity chromatography from soluble lysate and dialyzed overnight in 10 mM Tris-HCl, 20% glycerol, 1 mM 3-[(3-cholamidopropyl)dimethylammonio]-1-propanesulfonate (CHAPS), pH 8.5. The protease was concentrated through Vivaspin 20 centrifugal concentrator (GE Healthcare, Little Chalfont, UK) and stored at −80° C. The purified protein was detected by Western blot using anti-His-tag antibodies. Concentration of protein was determined by Bradford protein assay kit (Bio-Rad Laboratories, California, USA) using bovine serum albumin as standard.

Fluorescence-Based Protease Inhibition Assay

The recombinant ZIKV NS2B-NS3 protease was produced as previously described with some modifications (Lei et al., 2016). To detect ZIKV NS2B-NS3 protease activity, a fluorescence-based enzymatic assay was conducted in 96-well black micro-plates (Greiner Bio-One, Kremsmünster, Germany). A 7-amino-4-methylcoumarine substrate, Bz-Nle-Lys-Lys-Arg-AMC, was used (Lei et al., 2016). The fluorescence signal from the released AMC was measured at 460 nm with excitation at 360 nm, using a VICTOR™ X3 multilabel plate reader (Perkin Elmer, Massachusetts, USA). To detect if each drug inhibited ZIKV NS2B-NS3 protease activity, 5 nM ZIKV NS2B-NS3 protease and 10 μM substrate was fixed in the assay. ZIKV NS2B-NS3 protease was incubated for 10 min with different concentrations of compounds at 37° C. The mixtures of protease and individual drug were prepared in 50 μl reaction buffer and dispersed into each well, followed by the addition of 20 μM substrate in 50 μl buffer to initiate the cleavage. After 10 min, the fluorescence intensity was measured. The reaction and dilution buffer were consisted of 10 mM Tris-HCl, 20% glycerol, 1 mM CHAPS, 5% DMSO, pH 8.5. DMSO (5%) was included as a negative control.

Mouse Model and in Vivo Evaluation of Novobiocin Treatment

The in vivo treatment effect of novobiocin was evaluated in our recently established animal model for ZIKV infection using dexamethasone-immunosuppressed mice with disseminated ZIKV infection (Chan et al., 2016c). Approval was obtained from the Committee on the Use of Live Animals in Teaching and Research of The University of Hong Kong. Briefly, 6-8-week old male BALB/c mice were randomly divided into groups and given different regimens of virus inoculation, dexamethasone, and novobiocin treatment (Table 1). Phosphate-buffered saline (PBS) was used to dilute the virus stocks to the desired concentration, and inocula were back-titrated to verify the dose given. On the day of virus inoculation, a dose of the virus equivalent to $6×10^6$ $TCID_{50}$ ($3.24×10^6$ plaque forming units) in 2000 of PBS was inoculated via the intraperitoneal route into mice under ketamine (100 mg/kg) and xylazine (10 mg/kg) anesthesia. Mice in the negative-control groups were injected with the same volume of PBS. Mice were monitored three times each day for clinical signs of disease and a numerical score was assigned at each observation as previously described (Chan et al., 2016c). Three mice per group were sacrificed at 5 dpi for virological, histological, and immunohistochemistry analyses. The remaining mice were sacrificed at 14 dpi or euthanized when there was ≥20% weight loss or ≥10% weight loss with ≥1 clinical sign. Samples of major organs were collected at necropsy for virological, histological, and immunohistochemical analyzes as we previously described (Chan et al., 2016c. Chan et al., 2017b). Blood samples were also collected for RNA extraction and qRT-PCR analysis.

TABLE 1

Groups of mice receiving different regimens of virus inoculation, dexamethasone, and novobiocin treatment in this study[a].

| Group | Gender | Routes and inoculum of ZIKV (0 dpi) | Dexamethasone | Antiviral treatment | Date of sacrifice (number of mice) |
|---|---|---|---|---|---|
| 1 | M | ip 6 × 10 $TCID_{50}$ | 50 mg/kg q24 h ip, from 3 days before to 9 dpi inclusively | No | 5 (n = 3) and 12 (n = 5) dpi[b] |
| 2 | M | ip 6 × 10 $TCID_{50}$ | 50 mg/kg q24 h ip, from 3 days before to 9 dpi inclusively | Novobiocin 100 mg/kg q12 h sc at 1 dpi to 13 dpi inclusively | 5 (n = 3) and 14 (n = 5) dpi |
| 3 | M | No | 50 mg/kg q24 h ip, from 3 days before to 9 dpi inclusively | Novobiocin 100 mg/kg q12 h sc at 1 dpi to 13 dpi inclusively | 5 (n = 3) and 14 (n = 5) dpi |

[a]6-8 week-old BALB/c male mice were used in all the groups because more severe Zika virus disease is observed in male than female mice as we previously reported in this established animal model (Chraibi S., et al. *J Clin Virol* 83: 61-62; 2016).
[b]The mice in group 1 were euthanized at 12 dpi as they had ≥10% weight loss and ≥1 clinical symptom.
Abbreviations: dpi, days post-inoculation; ip, intraperitoneal; M, male; sc, subcutaneous.

Statistical Analyses

All statistical analyses were performed with GraphPad Prism software (GraphPad Software, Inc.). Kaplan-Meier survival curves were analyzed by the log-rank test. Student's t-test was used to determine significant differences in weight losses and virus titers among individual treatment groups as previously reported (Chan et al., 2016c). P-values<0.05 were considered statistically significant.

Example 1. In Silico Structure-Based Virtual Screening of Chemical Library and Molecular Docking All compounds deposited in the DrugBank v5.0.1 were set up for docking simulations by using Molecular Operating Environment v2008 (MOE, Chemical Computing Group Inc., Montreal, Canada) (Wishart et al., 2006). The crystal structure of the ZIKV-NS2B-NS3 protease (Protein Data Bank (PDB) code 5LC0) was used to build up the protein model system (Lei et al., 2016). Molecular parameters were calculated by removing salts and neutralizing their protonation state, computing partial charges by MMFF94 force field, adding hydrogen atoms and minimizing energies (default parameters) (Halgren, 1995). The crystal structure of the ZIKV-NS2B-NS3 protease (Protein Data Bank (PDB) code 5LC0) was used to build up the protein model system (Lei et al., 2016). At an early stage, bond orders were assigned, hydrogens were added, and cap termini were included with the Protein Preparation Wizard module as implemented in Maestro (Schrödinger Release 2016-4: Maestro, Schrödinger, LLC, New York, USA) (Sastry et al., 2013). Protonation states of all side chains were subsequently defined using PROPKA3.1. Partial charges over all atoms were finally assigned within the AMBER99 force field scheme as implemented in MOE v2008. Docking simulations were performed with Lead Finder software v1.1.16 (Stroganov et al., 2008). All docking parameters were set to default for the calculations. The best ranked docking score posed for every compound was retained for further analysis.

To identify potential inhibitors of the ZIKV-NS2B-NS3 protease, a total of 8227 entries from the DrugBank database were screened using Lead Finder software, in which the ZIKV-NS2B-NS3 protease crystal structure was utilized as inputs to the program (Lei et al., 2016) (FIG. 1). The top 100 primary hit compounds were ranked by their predicted binding affinities to the ZIKV-NS2B-NS3 protease (Table 2). In silico virtual screening of a chemical library with 8277 drug compounds was performed. Among the top 100 primary hit compounds with the highest predicted binding affinities with ZIKV-NS2B-NS3 protease, 8 clinically approved drugs belonging to different drug classes were selected for validation of anti-ZIKV-NS2B-NS3 protease activity. Other drug compounds were not selected because most of them were not clinically approved drugs, did not have well-known pharmacokinetic and pharmacodynamic properties, and/or belonged to the same drug classes as these 8 drugs (Table 2). Among them, 5 (62.5%) were demonstrated to have anti-ZIKV-NS2B-NS3 protease activity in a fluorescence-based enzymatic assay. Three of these 5 drugs which have high potentials for clinical use in pregnancy and/or patients with severe ZIKV-associated complications were then selected for further evaluation. The anti-ZIKV activity of these 3 drugs (novobiocin, lopinavir-ritonavir, and rifampicin) were then evaluated by viral load reduction, cytopathic effect inhibition, and/or plaque reduction assays. Novobiocin and lopinavir-ritonavir demonstrated anti-ZIKV activity in viral load reduction assay. Based on its higher selectivity index than lopinavir-ritonavir, novobiocin was then selected for further evaluation in a mouse model.

TABLE 2

Top 100 primary DrugBank hits identified by the Lead Finder software with the ZIKV-NS2B-NS3 protease as a target.

| DrugBank ID | Drug Compound Name |
|---|---|
| DB00035 | Desmopressin |
| DB00093 | Felypressin |
| DB00104 | Octreotide |
| DB00183 | Pentagastrin |
| DB00309 | Vindesine |
| DB00314 | Capreomycin |
| DB00416 | Metocurine Iodide |
| DB00471 | Montelukast |
| DB00503 | Ritonavir |
| DB00520 | Caspofungin |
| DB00565 | Cisatracurium besylate |
| DB00570 | Vinblastine |
| DB00646 | Nystatin |
| DB00732 | Atracurium besylate |
| DB00864 | Tacrolimus |
| DB00877 | Sirolimus |
| DB00947 | Fulvestrant |
| DB00954 | Dirithromycin |
| DB01045 | Rifampicin |
| DB01051 | Novobiocin |
| DB01135 | Doxacurium chloride |
| DB01199 | Tubocurarine |
| DB01201 | Rifapentine |
| DB01220 | Rifaximin |
| DB01226 | Mivacurium |
| DB01229 | Paclitaxel |
| DB01232 | Saquinavir |
| DB01248 | Docetaxel |
| DB01249 | Iodixanol |
| DB01282 | Carbetocin |
| DB01338 | Pipecuronium |
| DB01599 | Probucol |
| DB01663 | Lambda-Bis(2,2'-Bipyridine)-(5-Methyl-2-2'-Bipyridine)-C9-Adamantane Ruthenium (Ii) |
| DB01721 | Analogue of Indinavir Drug |
| DB01747 | Coprogen |

TABLE 2-continued

Top 100 primary DrugBank hits identified by the Lead Finder software with the ZIKV-NS2B-NS3 protease as a target.

| DrugBank ID | Drug Compound Name |
| --- | --- |
| DB01934 | N-Methyl-N-(10-Methylundecanoyl)-D-Seryl-L-Alanyl-N~1~-[(7s,10s,13s)-13-Carboxy-3,18-Dihydroxy-10-Methyl-8,11-Dioxo-9,12-Diazatricyclo[13.3.1.1~2,6~]Icosa-1(19),2(20),3,5,15,17-Hexaen-7-Yl]-N~1~-Methylglycinamide |
| DB01984 | 4-[2-(3-Benzyloxycarbonylamino-4-Cyclohexyl-1-Hydroxy-2-Oxo-Butylamino)-5-Guanidino-Pentanoylamino]-4-(1-Carboxy-2-Cyclohexyl-Ethylcarbamoyl)-Butyric Acid |
| DB02003 | Delta-Bis(2,2'-Bipyridine)Imidazole Ruthenium (Ii) |
| DB02092 | Cholesteryl Linoleate |
| DB02136 | Cephalosporin Analog |
| DB02169 | 9,10-Deepithio-9,10-Didehydroacanthifolicin |
| DB02226 | 3,8-Diamino-6-Phenyl-5-[6-[1-[2-[(1,2,3,4-Tetrahydro-9-Acridinyl)Amino]Ethyl]-1h-1,2,3-Triazol-4-Yl]Hexyl]-Phenanthridinium |
| DB02259 | 3-(3,5-Dibromo-4-Hydroxy-Benzoyl)-2-Ethyl-Benzofuran-6-Sulfonic Acid (4-Sulfamoyl-Phenyl)-Amide |
| DB02378 | MMI-175 |
| DB02460 | Hydrogenobyrinic Acid |
| DB02477 | [Cyclohexylethyl]-[[[[4-[2-Methyl-1-Imidazolyl-Butyl]Phenyl]Acetyl]-Seryl]-Lysinyl]-Amine |
| DB02555 | SP4160 |
| DB02581 | 5-[2,3-Dichloro-4-(5-{1-[2-(2-Guanidino-4-Methyl-Pentanoylamino)-Acetyl]-Piperidin-4-Yl}-1-Methyl-1h-Pyrazol-3-Yl)-Phenoxymethyl]-Furan-2-Carboxylic Acid |
| DB02638 | Terlipressin |
| DB02702 | XV638 |
| DB02704 | (2r,3r,4r,5r)-3,4-Dihydroxy-N,N'-Bis[(1s,2r)-2-Hydroxy-2,3-Dihydro-1h-Inden-1-Yl]-2,5-Bis(2-Phenylethyl)Hexanediamide |
| DB03021 | Ulapualide A |
| DB03063 | N-(1-Benzyl-3-{[3-(1,3-Dioxo-1,3-Dihydro-Isoindol-2-Yl)-Propionyl]-[2-(Hexahydro-Benzo[1,3]Dioxol-5-Yl)-Ethyl]-Amino}-2-Hydroxy-Propyl)-4-Benzyloxy-3,5-Dimethoxy-Benzamide |
| DB03208 | Beta-1,2,3,4,6-Penta-O-Galloyl-D-Glucopyranose |
| DB03232 | 2-[(2e,6e,10e,14e,18e,22e,26e)-3,7,11,15,19,23,27,31-Octamethyldotriaconta-2,6,10,14,18,22,26,30-Octaenyl]Phenol |
| DB03276 | 4-[(10s,14s,18s)-18-(2-Amino-2-Oxoethyl)-14-(1-Naphthylmethyl)-8,17,20-Trioxo-7,16,19-Triazaspiro[5.14]Icos-11-En-10-Yl]Benzylphosphonic Acid |
| DB03311 | 3-(3,5-Dibromo-4-Hydroxy-Benzoyl)-2-Ethyl-Benzofuran-6-Sulfonic Acid [4-(Thiazol-2-Ylsulfamoyl)-Phenyl]-Amide |
| DB03395 | Enalkiren |
| DB03492 | Lambda-Bis(2,2'-Bipyridine)Imidazole Osmium (Ii) |
| DB03616 | Kabiramide C |
| DB03621 | L-709,587 |
| DB03648 | 2-{N'-[2-(5-Amino-1-Phenylcarbamoyl-Pentylcarbamoyl)-Hexyl]-Hydrazinomethyl}-Hexanoic Acid(5-Amino-1-Phenylcarbamoyl-Pentyl)-Amide |
| DB03850 | Jaspisamide A |
| DB03871 | Lambda-Bis(2,2'-Bipyridine)Imidazole Ruthenium (Ii) |
| DB03875 | Delta-Bis(2,2'-Bipyridine)-(5-Methyl-2-2'-Bipyridine)-C9-Adamantane Ruthenium (Ii) |
| DB03932 | LFA703 |
| DB03933 | C-1027 Aromatized Chromophore |
| DB04042 | 2-[4-(Hydroxy-Methoxy-Methyl)-Benzyl]-7-(4-Hydroxymethyl-Benzyl)-1,1-Dioxo-3,6-Bis-Phenoxymethyl-1lambda6-[1,2,7]Thiadiazepane-4,5-Diol |
| DB04124 | Aurodox |
| DB04220 | Rifamycin Cgp 4832 |
| DB04269 | Cyclotheonamide A |
| DB04348 | Taurocholic Acid |
| DB04408 | Ncs-Chromophore |
| DB04547 | Bea409 |
| DB04550 | Delta-Bis(2,2'-Bipyridine)Imidazole Osmium (Ii) |
| DB04606 | 2-[2-ETHANESULFONYLAMINO-3-(5-PROPOXY-1H-INDOL-3-YL)-PROPIONYLAMINO]-PENTANEDIOIC ACID 5-AMIDE 1-(4-CARBAMIMIDOYL-BENZYLAMIDE) |
| DB04629 | Aplyronine A |
| DB04697 | TRANS-4-(GUANIDINOMETHYL)-CYCLOHEXANE-L-YL-D-3-CYCLOHEXYLALANYL-L-AZETIDINE-2-YL-D-TYROSINYL-L-HOMOARGININAMIDE |
| DB04711 | Iodipamide |
| DB04738 | Motuporin |
| DB04741 | Myxothiazol |
| DB04748 | OXIMINOARYLSULFONAMIDE |
| DB04774 | Reidispongiolide A |
| DB04775 | Reidispongiolide C |

TABLE 2-continued

Top 100 primary DrugBank hits identified by the Lead Finder
software with the ZIKV-NS2B-NS3 protease as a target.

| DrugBank ID | Drug Compound Name |
|---|---|
| DB04785 | Streptolydigin |
| DB04869 | Olcegepant |
| DB04877 | Voacamine |
| DB04894 | Vapreotide |
| DB04972 | Canfosfamide |
| DB05128 | Aminocandin |
| DB05296 | Motexafin lutetium |
| DB05297 | DHA-paclitaxel |
| DB05399 | AGI-1067 |
| DB05403 | CEP-1347 |
| DB05428 | motexafin gadolinium |
| DB05434 | ABT-510 |
| DB05465 | MLN-518 |
| DB05868 | BILN 2061 |
| DB06287 | Temsirolimus |
| DB06290 | Simeprevir |
| DB06419 | Cethromycin |
| DB06439 | Tyloxapol |
| DB06636 | Isavuconazonium |
| DB06663 | Pasireotide |
| DB06695 | Dabigatran etexilate |
| DB06749 | Ginsenoside Rb1 |
| DB06750 | Ginsenoside Rg1 |
| DB06772 | Cabazitaxel |
| DB06827 | Viomycin |
| DB07165 | N-(5-CHLORO-BENZO[B]THIOPHEN-3-YLMETHYL)-2-[6-CHLORO-OXO-3-(2-PYRIDIN-2-YL-ETHYLAMINO)-2H-PYRAZIN-1-YL]-ACETAMIDE |
| DB07169 | 5R-(3,4-DICHLOROPHENYLMETHYL)-3-(2-THIOPHENESULFONYLAMINO)-4-OXO-2-THIONOTHIAZOLIDINE |
| DB08823 | Spinosad |
| DB08834 | Tauroursodeoxycholic acid |
| DB08871 | Eribulin |
| DB08993 | Enviomycin |
| DB09065 | Cobicistat |
| DB09102 | Daclatasvir |
| DB09134 | Ioversol |
| DB09204 | Arotinolol |
| DB09270 | Coenzyme Q10 |
| DB09296 | Ombitasvir |
| DB09297 | Paritaprevir |
| DB09313 | Ioxaglic acid |
| DB11575 | Grazoprevir |
| DB11581 | Venetoclax |

Example 2. Validation of ZIKV-NS2B-NS3 Protease Inhibition by Primary Hit Compounds Belonging to Different Drug Classes To verify whether the primary hit compounds inhibited ZIKV-NS2B-NS3 protease activity, we selected 8 clinically approved drugs that belong to different drug classes (i.e. desmopressin acetate, lopinavir-ritonavir, montelukast, novobiocin, octreotide acetate, rifampicin, sirolimus, and tacrolimus) for further evaluation. Other drug compounds were not selected because most of them were not clinically approved drugs, did not have well-known pharmacokinetic and pharmacodynamic properties, and/or belonged to the same drug classes as these 8 drugs. We performed a fluorescence-based protease inhibition assay that recorded fluorescence signals in the presence or absence of the drugs. To detect the enzymatic activity of the purified ZIKV-NS2B-NS3 protein, we first used four concentrations of the protease substrate (0.1 µM, 10 µM, and 100 µM) for comparison and observed a dose-dependent increase of fluorescence intensity upon protein addition to the substrate. FIG. 2A shows the protein dose-dependent fluorescence intensities, indicating the cleavage of the fluorescent substrate (Bz-Nle-Lys-Lys-Arg-AMC) by the protein. Four concentrations of the substrate (100 µM, 10 µM, and 0.1 µM) were tested for the purpose of assay optimization. A pET32a(+)-blank protein, incubated with 100 µM substrate, was included as a mock-purified enzyme control. Results are shown as the number of fold changes of fluoresence intensity after ZIKV-NS2N-NS3 protein was added as compared to the baseline level. Cleavage of the peptide substrate released fluorescence signals, which reached a plateau when 50 nM protein was added. Compared to the baseline control, as much as a 25-fold increase in fluorescence intensity was detected with input of 10 µM and 100 µM substrate. These results suggested that the purified ZIKV-NS2B-NS3 protein maintained protease activity.

Figure 2B:
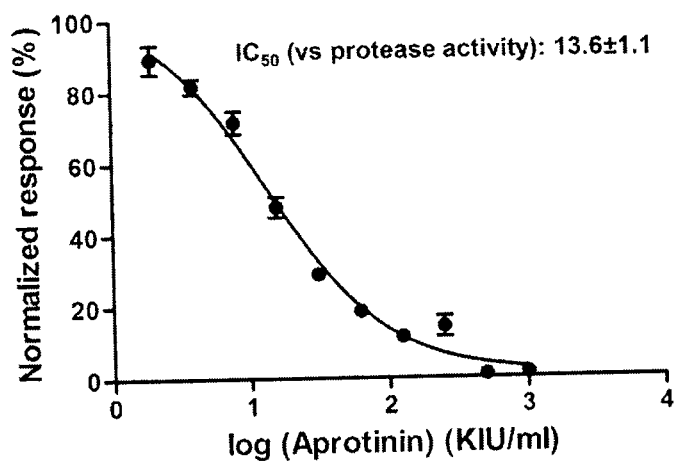
Figure 2C:
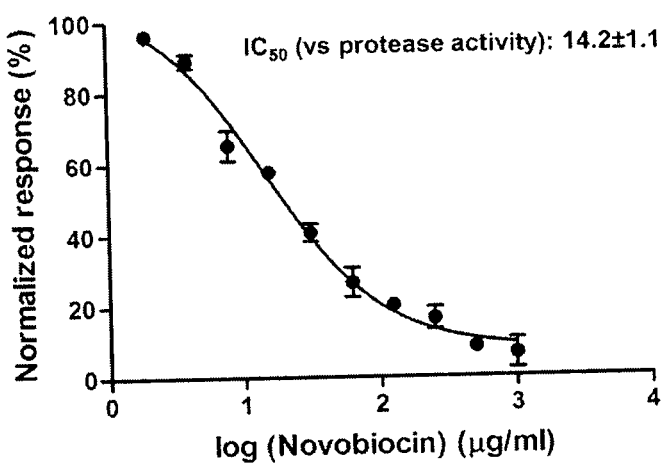
Figure 3A:
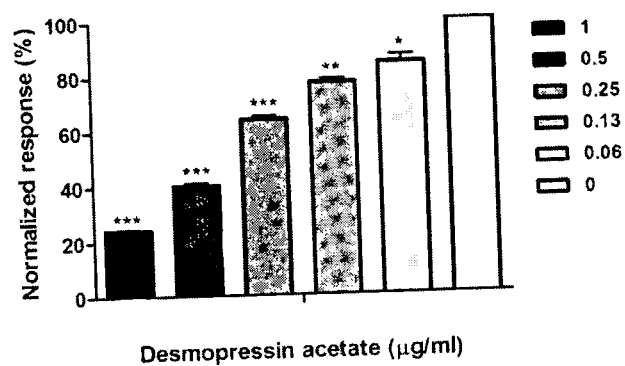
FIGS. 3A-3G are graphs of normalized response (% inhibition of ZIKV-NS2B-NS3 protease activity) versus different concentrations of different compounds. In the protease inhibition assay, concentrations of the substrate and ZIKV NS2B-NS3 protease were fixed as 10 µM and 5 nM, respectively, while increasing concentrations of (FIG. 3A) desmopressin acetate, (FIG. 3B) octreotide acetate, (FIG. 3C) lopinavir-ritonavir, (FIG. 3D) rifampicin, (FIG. 3E) montelukast, (FIG. 3F) sirolimus, and (FIG. 3G) tacrolimus were added. Data in each panel is normalized as the percentage to the untreated group * denotes P<0.05 and ** denotes P<0.01 (compared to the DMSO control group by Student's t test). Results are presented as mean values plus standard error of the mean (error bars). The experiments were carried out in triplicate and repeated twice for confirmation.
Figure 3B:
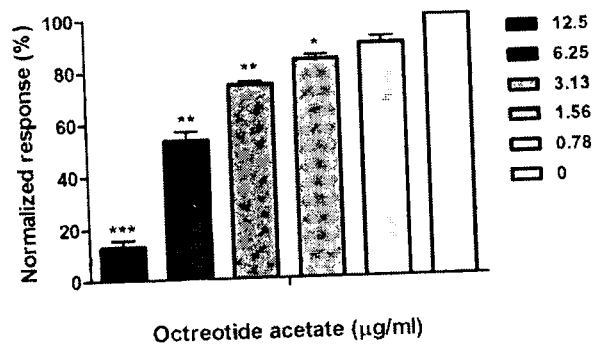
Figure 3C:
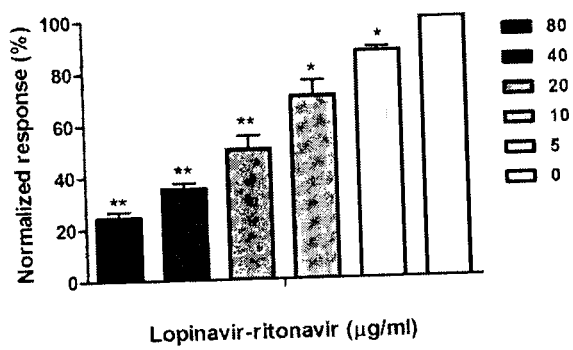
Figure 3D:
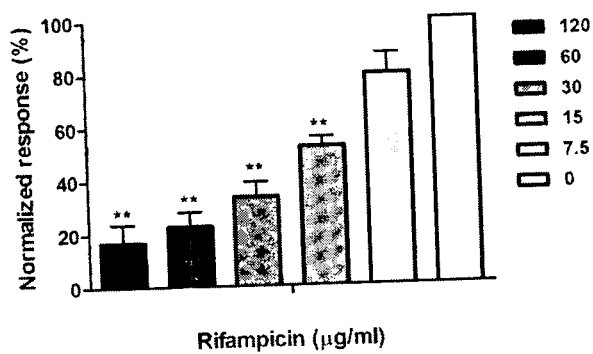
Figure 3E:
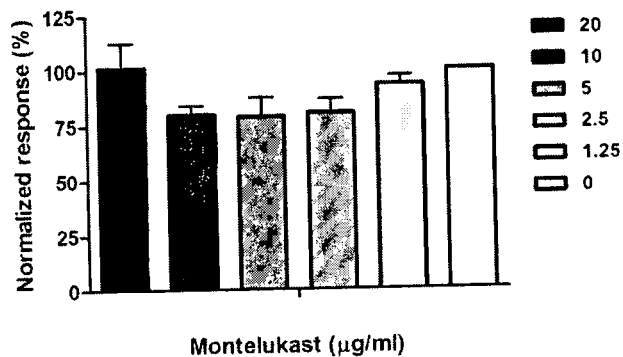
Figure 3F:
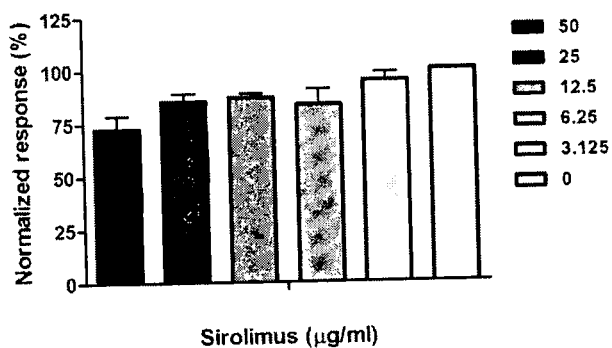
Figure 3G:
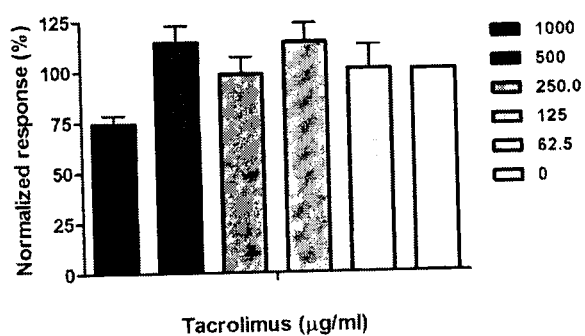

To detect the inhibitory effect of the drugs on ZIKV-NS2B-NS3 protease activity, we measured fluorescence signals in the presence of a range of different concentrations of the drugs, using aprotinin as a positive control (FIG. 2B) (Phoo et al., 2016). At the fixed concentration of 10 µM substrate and 5 nM ZIKV-NS2B-NS3 protease, we observed a dose-dependent reduction in protease activity with increasing concentrations of 5 of the 8 (62.5%) drugs, including novobiocin (FIG. 2C), desmopressin acetate, octreotide acetate, lopinavir-ritonavir, and rifampicin (FIGS. 3A-3G and Table 3). In FIGS. 2B and 2C, it is demonstrated that increasing concentrations of aprotinin (positive control) and novobiocin blocked the protease cleavage activity as measured by the decrease in fluorescence intensity values. The concentrations of substrate and ZIKV-NS2B-NS3 protease were fixed as 10 µM and 5 nM, respectively. Our results confirmed that these drugs inhibited ZIKV-NS2B-NS3 protease activity and that the in silico virtual screening was useful in predicting potential ZIKV-NS2B-NS3 protease inhibitors.

TABLE 3

Summary of the $IC_{50}$ of each drug against ZIKV NS2B-NS3 protease activity.

| Drug | $IC_{50}$ (vs protease activity) | Unit |
|---|---|---|
| Aprotinin | 13.6 ± 1.1 | KIU/ml |
| Desmopressin acetate | 505.1 ± 1.3 | µg/ml |
| Lopinavir-ritonavir | 20.4 ± 3.3 | µg/ml |
| Novobiocin | 14.2 ± 1.1 | µg/ml |
| Octreotide acetate | 8.1 ± 0.9 | µg/ml |
| Rifampicin | 14.5 ± 1.3 | µg/ml |
| Montelukast | — | — |
| Sirolimus | — | — |
| Tacrolimus | — | — |

"—" indicates no inhibition. $IC_{50}$, half maximal inhibitory concentration (concentration of the drug at which there was 50% reduction in protease activity).

Figure 4A:
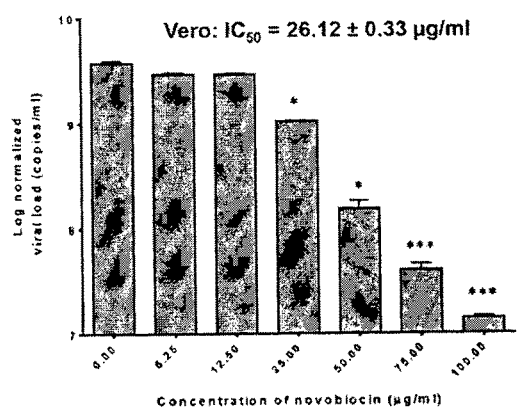
FIGS. 4A-4C are graphs showing the evaluation of the in vitro anti-ZIKV activity of novobiocin.
Figure 4B:
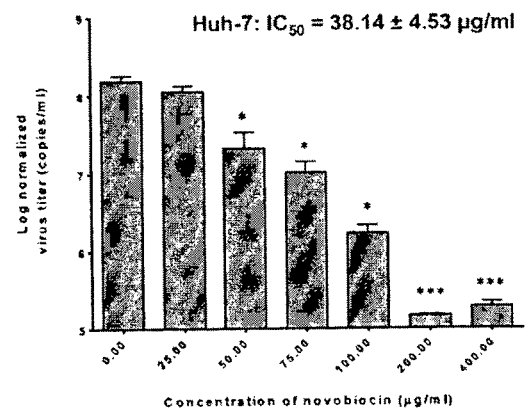
Figure 4C:
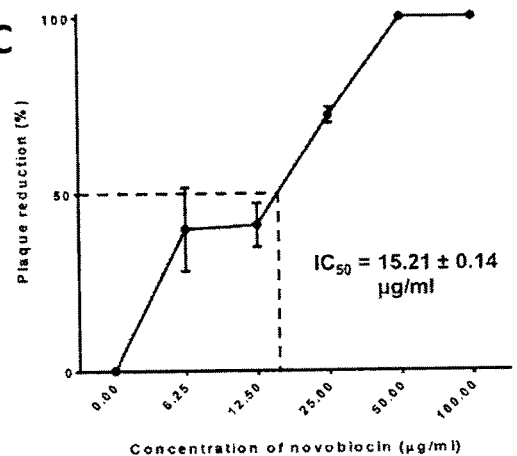
Figure 5A:
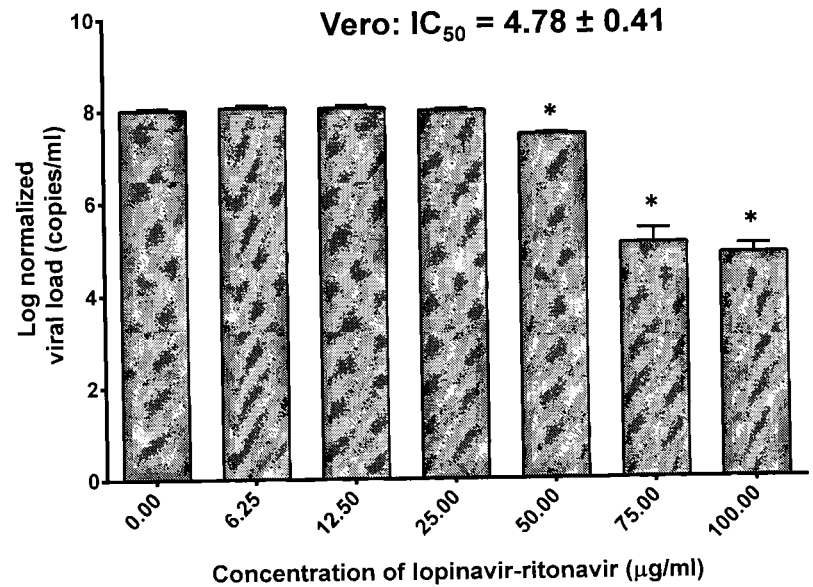
FIGS. 5A and 5B are graphs showing the in vitro anti-ZIKV activity of lopinavir-ritonavir.
Figure 5B:
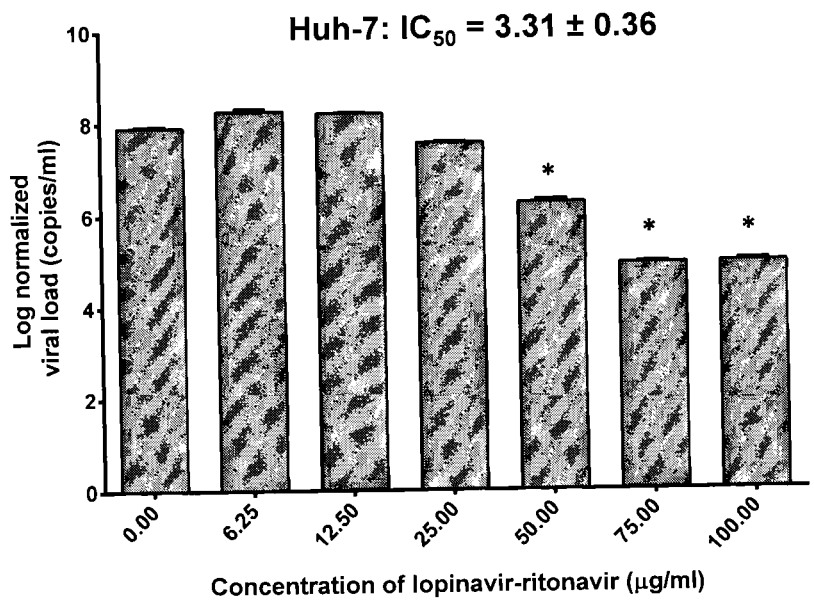

Example 3. Validation of the in Vitro Anti-ZIKV Activity of Selected ZIKV-NS2B-NS3 Protease Inhibitors Among the validated ZIKV-NS2B-NS3 protease inhibitors, we further selected three clinically approved drugs with good side effect profiles that could potentially be used in pregnant patients and/or patients with severe ZIKV-associated complications (novobiocin, lopinavir-ritonavir, and rifampicin) for in vitro anti-ZIKV activity testing. Cytotoxicity and antiviral potency of the drugs were evaluated in two different cell lines (Vero and Huh-7 cells) that could robustly support ZIKV replication (Chan et al., 2016b). The 50% effective cytotoxic concentrations ($CC_{50}$) of novobiocin, lopinavir-ritonavir, and rifampicin in Vero cells were 850.50 µg/ml, 30.00 µg/ml, and 400.00 µg/ml, respectively, while in Huh-7 cells, 1103.184 ml, 32.12 µg/ml, and 400.00 µg/ml, respectively. In the viral load reduction assay, dose-dependent reduction in virus titer was observed in novobiocin-treated (half maximal inhibitory concentration ($IC_{50}$)=26.12±0.33 µg/ml in Vero cells and 38.14±4.53 µg/ml in Huh-7 cells) and lopinavir-ritonavir-treated ($IC_{50}$=4.78±0.41 µg/ml in Vero cells and 3.31±0.36 µg/ml in Huh-7 cells) (FIGS. 4A, 4B, 5A, and 5B), but not rifampicin-treated culture supernatants (data not shown). In FIG. 4A, ZIKV viral load reduction is quantified by quantitative reverse transcription-polymerase chain reaction (qRT-PCR) in Vero cells at 48 hours after ZIKV inoculation (0.05 MOI) with novobiocin. In FIG. 4B, ZIKV viral load reduction is quantified by qRT-PCR in Huh-7 cells at 48 hours after ZIKV inoculation (0.05 MOI) with novobiocin. The mean virus titer was significantly reduced (P<0.05) at ≥25.00 µg/ml of novobiocin and at ≥50.00 µg/ml of lopinavir-ritonavir. Given the higher selectivity index ($CC_{50}/IC_{50}$) of novobiocin (28.92-32.56) than lopinavir-ritonavir (6.28-9.70), we further validated the anti-ZIKV activity of novobiocin in cytopathic effect (CPE) inhibition and plaque reduction assays. In the CPE inhibition assay, novobiocin protected Vero cells from developing ZIKV-induced CPE ($IC_{50}$=53.26±2.48 µg/ml). In the plaque reduction assay, novobiocin achieved 100% plaque reduction at concentrations ≥50.00 µg/ml ($IC_{50}$=15.21±0.14 µg/ml) (FIG. 4C). Half maximal inhibitory concentration ($IC_{50}$) of novobiocin as determined by plaque reduction assay are shown in FIG. 4C.

Example 4. Treatment with Novobiocin Improved Clinical Outcome of Dexamethasone-Immunosuppressed Mice with Disseminated ZIKV Infection Extending from the in silico and in vitro findings, we further evaluated the in vivo therapeutic effects of novobiocin in our recently established animal model of dexamethasone-immunosuppressed mice with disseminated ZIKV infection (Chan et al., 2016c). We treated the dexamethasone-immunosuppressed mice with subcutaneous novobiocin 100 mg/kg q12 h from 1-13 day-post-infection (dpi) as they tolerated this dosage well without developing clinical symptoms and had weight loss of <5% (FIG. 6A).

Figure 6B:
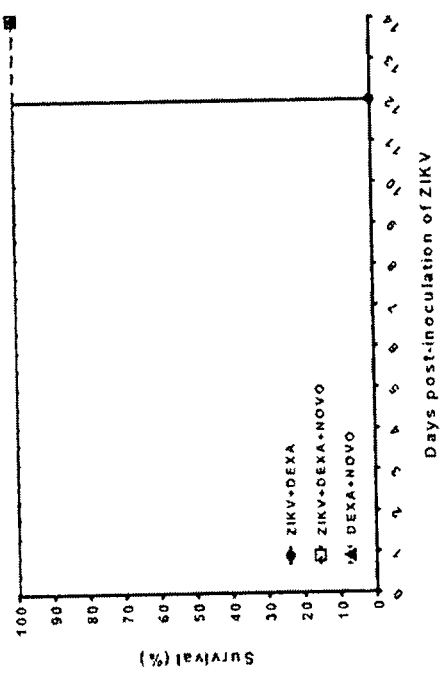
FIGS. 6A-6C are graphs showing the evaluation of the in vivo anti-ZIKV activity of novobiocin.
Figure 6C:
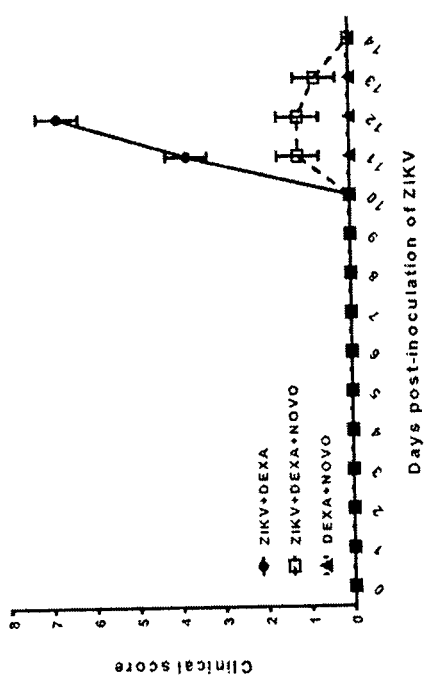
Figure 6A:
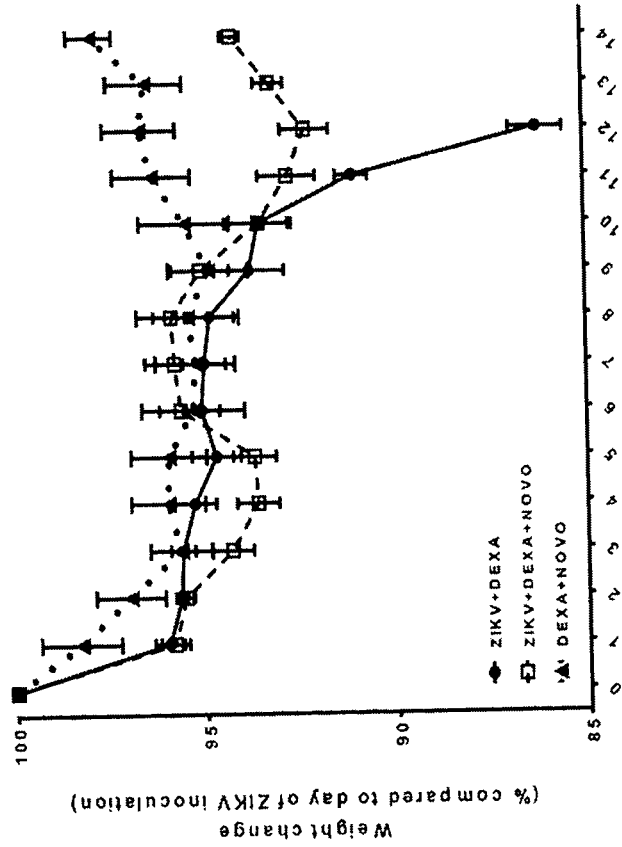

FIG. 6A shows ZIKV viral load reduction quantified by quantitative reverse transcription-polymerase chain reaction (qRT-PCR) in Vero cells at 48 hours after ZIKV inoculation (0.05 MOI) with novobiocin. FIG. 6B shows ZIKV viral load reduction quantified by qRT-PCR in Huh-7 cells at 48 hours after ZIKV inoculation (0.05 MOI) with novobiocin. FIG. 6C shows half maximal inhibitory concentration ($IC_{50}$) of novobiocin as determined by plaque reduction assay. All experiments were performed in triplicates and repeated twice for confirmation. * denotes P<0.05 and *** denotes P<0.0001 (compared to the DMSO control group by Student's t test). Data are presented as mean values±standard error of the mean (error bars).

Higher dosages (150 mg/kg q12 h or 200 mg/kg q12 h) of novobiocin led to the development of lethargy, poor feeding, and body weight loss of >10% among the mice after 6-8 days of treatment and were therefore not used in our in vivo treatment study. Consistent with our previous findings, the control mice with dexamethasone-immunosuppression and ZIKV inoculation developed ≥10% body weight loss with high clinical scores soon after dexamethasone withdrawal (10 dpi), which warranted euthanasia of all the mice at 12 dpi (FIGS. 6A-6C).

The treatment efficacy of novobiocin for ZIKV infection was also evaluated. In contrast to the untreated control mice which developed disseminated ZIKV infection with abundant ZIKV NS1 antigen expression in organ tissues (brain, testis, and kidney) and collected at 5 dpi and clinical deterioration with multiorgan inflammation soon after dexamethasone withdrawal at 10 dpi warranting euthanasia at 12 dpi, novobiocin-treated mice had minimal ZIKV NS1 antigen expression in their organ tissues collected at 5 dpi and little inflammatory infiltrate upon dexamethasone withdrawal at 12 dpi. There were significantly reduced mean viral loads in the blood and the major organ tissues, including the testis and kidney which are important in the transmission of ZIKV, during both early (5 dpi) and late (14 dpi) stages of infection. Although novobiocin's penetration into the central nervous system through non-inflamed meninges may be limited, the early control of viremia and penetration of the drug through possibly inflamed meninges likely contributed to the improved clinical outcome of the novobiocin-treated mice.

For immunohistochemical analysis, each organ was entirely embedded in one paraffin block, and one full-face paraffin section at the maximum diameter of each organ was examined per block. Marked inflammatory infiltration with distorted tissue architecture could be seen in the brain, testis, and kidney of the dexamethasone-immunosuppressed mice with ZIKV inoculation without novobiocin treatment. The mice with ZIKV-inoculation with novobiocin treatment and the control mice with mock infection and novobiocin treatment had no or mild inflammatory infiltrate, and preserved tissue architecture.

Immunohistochemical (5 dpi) and hematoxylin and eosin (H&E) (12 dpi) staining of the major organ tissues of these mice showed abundant ZIKV-NS1 antigen expression and marked inflammatory infiltrates, respectively. In contrast, all the novobiocin-treated, dexamethasone-immunosuppressed mice with ZIKV inoculation survived and developed ≤8% weight loss with minimal clinical symptoms after dexamethasone withdrawal which gradually recovered at 13-14 dpi (survival, 100% novobiocin-treated mice vs 0% untreated control mice, $P<0.05$). Corroborating with the clinical parameters, ZIKV-NS1 antigen expression was rarely detected by immunohistochemical staining in the organs (5 dpi) and minimal inflammatory infiltrates were seen in H&E-stained tissues (14 dpi) of these novobiocin-treated mice. The absence of ZIKV-NS1 antigen expression in immunohistochemical staining and inflammatory infiltrates in H&E staining in the organ tissues of the mock-infected control mice with dexamethasone immunosuppression and novobiocin treatment indicated that these changes were not due to drug-induced effects.

Figure 7A:
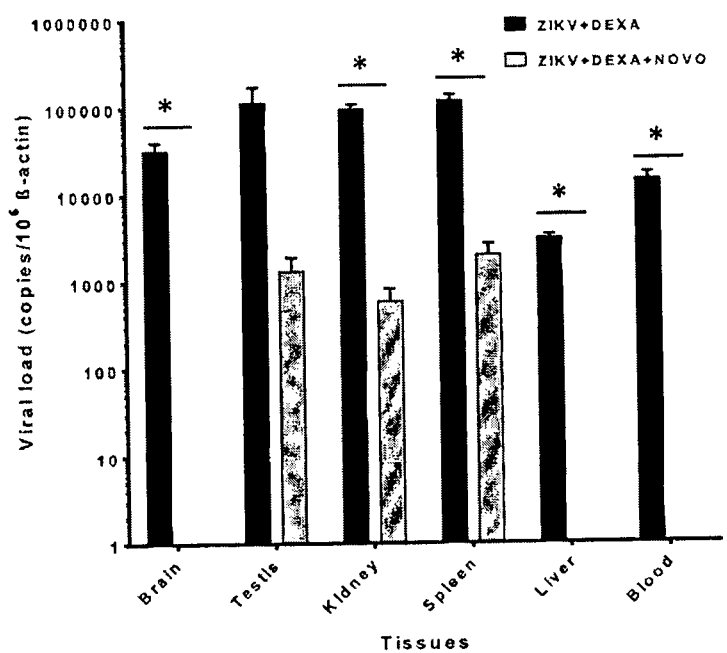
FIGS. 7A and 7B are graphs of viral loads in the blood and major organs of different groups of mice in the in vivo studies. * denotes P-values of <0.05. Data are presented as mean values±standard error of the mean (error bars). Abbreviations: DEXA, dexamethasone; NOVO, novobiocin; ZIKV, Zika virus.
Figure 7B:
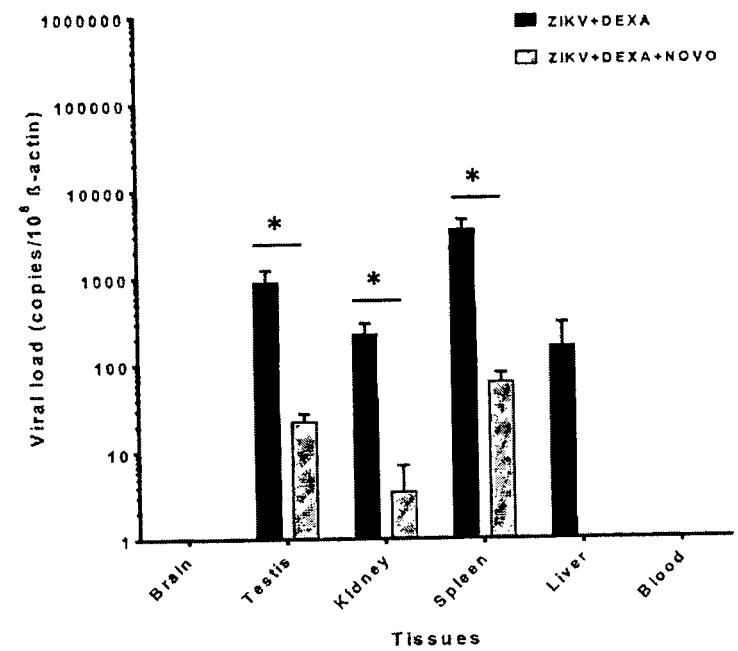

FIGS. 7A and 7B show that mice with novobiocin treatment had reduced ZIKV blood and tissue viral loads as compared to untreated mice at 5 days post-ZIKV inoculation (n=3 per group from two independent experiments) (FIG. 7A) and 14 days days post-ZIKV inoculation (n=5 per group from two independent experiments) (FIG. 7B). ZIKV RNA copies in the blood and tissues of the mice were determined by qRT-PCR and normalized by β-actin. The mean viral loads of the blood and most major organ tissues of the novobiocin-treated mice were significantly lower than those of the untreated control mice (with ≥2-log reduction) at both 5 dpi and 14 dpi (FIGS. 7A and 7B).

Figure 8:
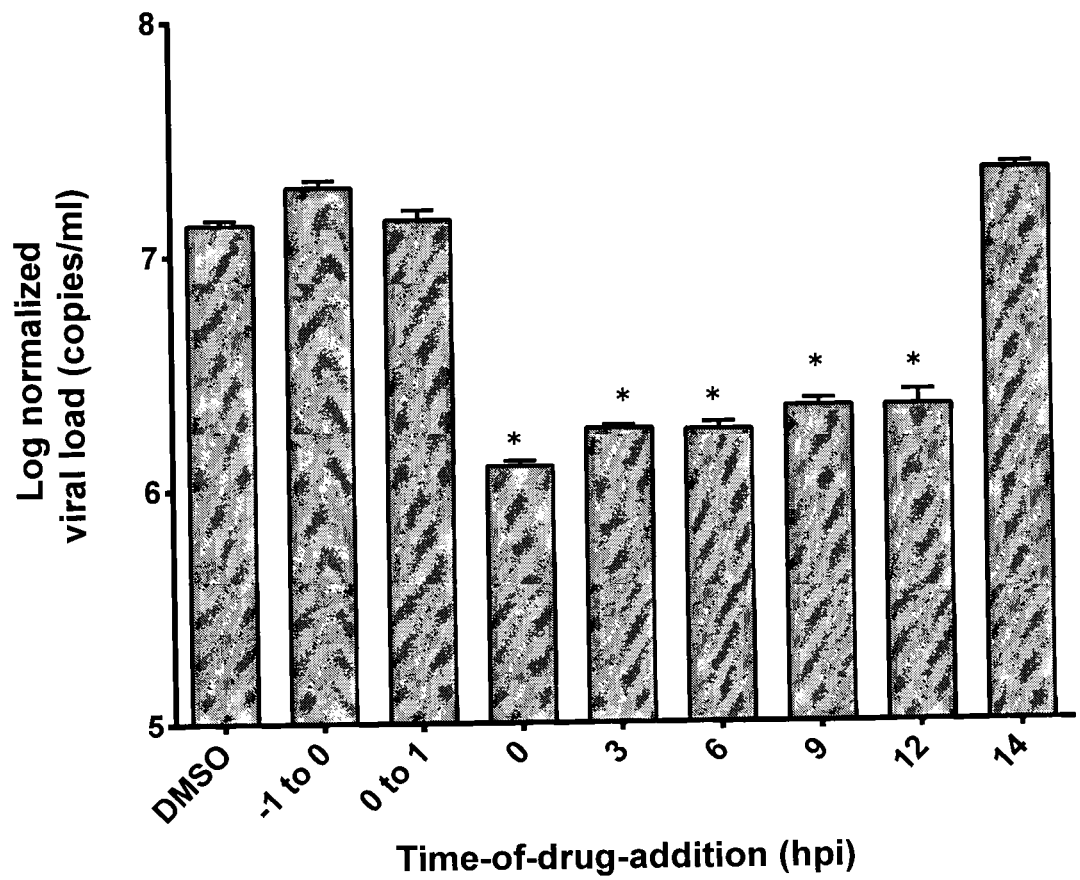
FIG. 8 is a graph of log normalized viral load versus time-of-drug-addition for novobiocin.

Example 5. Novobiocin Inhibited the Post-Entry Events of ZIKV Replication Cycle To investigate the phase of the ZIKV replication cycle interrupted by novobiocin, we performed a time-of-drug-addition assay by exposing ZIKV-infected cells to novobiocin at different time points during the virus replication cycle, followed by measurement of virus titers at 18 hours post-inoculation (hpi). Vero cells were infected by 2 multiplicity of infection (MOI) of ZIKV, when novobiocin was added during the virus replication stage (0, 3, 6, 9, or 12 hpi), viral loads were significantly reduced ($P<0.05$) within 12 h (FIG. 8). No significant inhibitory activity was observed when novobiocin was added at the virus adsorption stage (0-1 hpi) or at the release stage (14 hpi). ZIKV attachment was also not affected when the Vero cells were pretreated with novobiocin (−1 to 0 hpi). As the duration of a single ZIKV life cycle has been previously determined to be around 12-14 h, in which the onset of intracellular viral RNA production occurs at ~10-12 hpi, and progeny virions are assembled and released after 12 hpi (Zmurko et al., 2016; Chan et al., 2017a), our time-of-drug-addition results indicated that novobiocin interfered with post-entry events during the ZIKV replication cycle within stages after virus internalization and prior to budding.

Figure 9B:
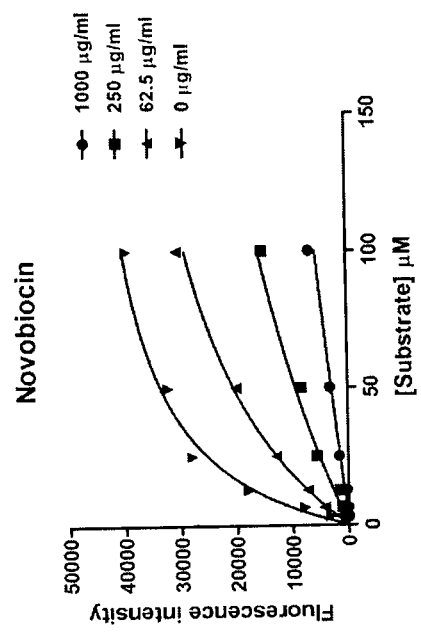
FIG. 9B is a graph showing the competitive mode of protease inhibition of novobiocin. In the assay, concentration of ZIKV NS2B-NS3 protease was fixed as 5 nM, while different concentrations of substrate (100, 50, 25, 12.5, 6.25, 3.125 and 0 μM) were added to plot the enzyme kinetic curves. Four concentrations of the drug (1000, 250, 62.5 and 0 μg/ml) were tested individually against the different concentrations of substrate. The experiments were repeated twice for confirmation. The data were analyzed for mode of inhibition by GraphPad Prism 6 in the module of enzyme kinetics. $R^2 > 0.95$ was considered as statistically significant.
Figure 9A:
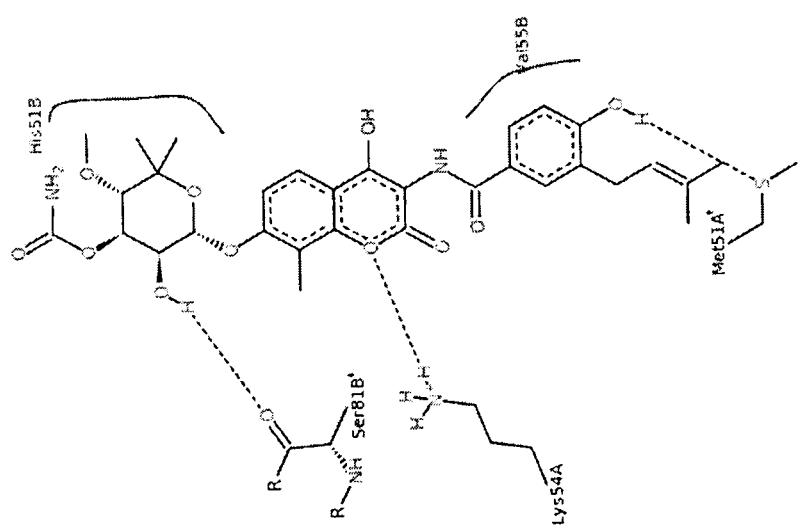
FIG. 9A illustrates the molecular model of novobiocin docked with ZIKV NS2B-NS3 in a two-dimensional representation of the protein-ligand interactions between novobiocin and ZIKV NS2B-NS3. Hydrogen bonds and hydrophobic contact areas are represented by dashed lines and the two brackets, respectively. The main interacting residues are labeled. The dashed lines represent bonds between hydrogen and acceptor atoms that are involved.

Example 6. Novobiocin was Predicted to Interact with the Key Enzymatic Sites of the ZIKV-NS2B-NS3 Protease To better characterize the structural interactions between novobiocin and the ZIKV-NS2B-NS3 protease, molecular docking was performed to predict the binding site of novobiocin within the ZIKV-NS2B-NS3 protein. As shown in FIG. 9A, three hydrogen bonds were formed between the ligand and the protein through residues MET51* (*denotes ZIKV-NS2B residues), SER81*, and LYS54, and broad areas of hydrophobic stabilization were formed between the compound and residues HIS51 and VAL155. Interestingly, two of these predicted interacting residues (SER81* and HIS51) were also identified as contacting residues between the boronate inhibitor cn-716 and the ZIKV-NS2B-NS3 protease protein in another report (Lei et al., 2016). This result suggested that novobiocin, like the protease inhibitor cn-716, might also impair the ZIKV-NS2B-NS3 catalytic efficiency. To explore the mode of protease inhibition, enzyme kinetic experiments were performed in the presence or absence of the drug. As shown in FIG. 9B, novobiocin appeared as a competitive ZIKV NS2B-NS3 protease inhibitor (global $R^2=0.99$). Molecular dynamics simulations provided additional insights into the stability of the novobiocin-ZIKV-NS2B-NS3 complex and showed that the geometrical fluctuations associated with the drug-protein binding were quickly stabilized. Overall, these findings suggested that the binding of novobiocin to its binding pocket at ZIKV-NS2B-NS3 was highly stable and that the drug potentially inhibited ZIKV-NS2B-NS3 protease activity by diminishing its catalytic efficiency.

Example 7. Successful Prevention and/or Treatment of ZIKA Virus Infection in an in Vivo Animal Model The recent identification of bromocriptine as an anti-ZIKV inhibitor validated ZIKV-NS2B-NS3 protease as a druggable target for the development of Zika therapeutics (Chan et al., 2017a). In the instant application, an in silico structure-based approach was adopted to rapidly screen a large chemical library and numerous other clinically approved drugs with inhibitory activity on the ZIKV-NS2B-NS3 protease were identified. The anti-ZIKV activity of novobiocin was further validated in multiple in vitro antiviral assays and in an immunodeficient mouse model. Novobiocin, also known as albamycin or cathomycin, is an aminocoumarin antibiotic that exerts its antibacterial effects (mainly against *Staphylococcus* sp.) by targeting the GyrB subunit of bacterial DNA gyrase to competitively inhibit the adenosine triphosphatase reaction catalyzed by GyrB (Kirby et al., 1956). The inhibitory activity of novobiocin on the replication of various DNA viruses, including herpesviruses (herpes simplex virus, cytomegalovirus, Epstein-Barr virus, Kaposi sarcoma-associated herpes virus, and vaccinia virus), simian virus 40, and duck hepatitis B virus, have been previously described (Civitico et al., 1990; Droge et al., 1985; Furlini et al., 1983; Gonzalez-Molleda et al., 2012; Pessina et al., 1992; Sekiguchi et al., 1997; Wu et al., 2014). The proposed antiviral mechanism of novobiocin against these DNA viruses is via blockade of host topoisomerases to inhibit viral replication and assembly (Sekiguchi et al., 1997; Wu et al., 2014). Our findings described a novel mechanism by which novobiocin inhibited the replication of an RNA virus belonging to the Flaviviridae.

Molecular docking and molecular dynamics simulations indicated that the binding between novobiocin and ZIKV-NS2B-NS3 was highly stable. The HIS51 residue predicted to be interacting with novobiocin is a highly-conserved catalysis residue of ZIKV-N2SB-NS3 protease activity (Phoo et al., 2016). These results suggested that novobiocin may provide cross-protection against different ZIKV subtypes/strains. The functional fluorescence-based protease inhibition assay confirmed that novobicin inhibited ZIKV-NS2B-NS3 protease activity. The ZIKV-NS2B-NS3 protease is an attractive antiviral target because it plays a pivotal role in processing the viral polyprotein to generate structural and non-structural viral proteins during viral replication (Zhu et al., 2016).

The treatment efficacy of novobiocin for ZIKV infection was also evaluated in our recently established mouse model (Chan et al., 2016c). In contrast to the untreated control mice which developed disseminated ZIKV infection with abundant ZIKV-NS1 antigen expression in organ tissues collected at 5 dpi and clinical deterioration with multiorgan inflammation soon after dexamethasone withdrawal at 10 dpi warranting euthanasia at 12 dpi, novobiocin-treated mice had minimal ZIKV-NS1 antigen expression in their organ tissues collected at 5 dpi and little inflammatory infiltrate upon dexamethasone withdrawal at 12 dpi. There were significantly reduced mean viral loads in the blood and the major organ tissues, including the testis and kidney which are important in the transmission of ZIKV, during both early (5 dpi) and late (14 dpi) stages of infection. Although novobiocin's penetration into the central nervous system through non-inflamed meninges may be limited, the early control of viremia and penetration of the drug through possibly inflamed meninges likely contributed to the improved clinical outcome of the novobiocin-treated mice.

Novobiocin was withdrawn from sale in the United States in 2011 because it was no longer considered an effective antibacterial agent, as numerous other newer anti-staphylococcal antibiotics became available. Nevertheless, treatment with novobiocin is generally well tolerated clinically and may be considered in pregnant women if the potential benefits outweigh the side effects (FDA pregnancy category C) (Kirby et al., 1956). A few other clinically approved drugs that are non-immunosuppressive and belong to FDA pregnancy categories B or C have also recently been reported to have in vitro anti-ZIKV effects. These included azithromycin, chloroquine, daptomycin, ivermectin, mefloquine, niclosamide, and sofosbuvir (Barrows et al., 2016; Bullard-Feibelman et al., 2016; Delvecchio et al., 2016; Retallack et al., 2016; Xu et al., 2016). However, except for sofosbuvir, none of these has been proven to be effective in animal models (Bullard-Feibelman et al., 2016). Importantly, most of these drugs have $IC_{50}$ values that are not achievable by routine oral therapeutic dosages. The Cmax: $IC_{50}$ ratio achievable with routine therapeutic dosage of oral novobiocin (1.17-4.11) is markedly higher than those of oral mefloquine (0.58), oral ivermectin (0.30), oral azithromycin (0.26), and oral chloroquine (0.12) (Barrows et al., 2016; Drusano et al., 1986; Retallack et al., 2016; Xu et al., 2016). Oral and parenteral niclosamide are insoluble (Zhang et al., 2015). Daptomycin is only available for intravenous administration. Sofusovir is expensive (≥1000 USD/tablet). Moreover, the mechanisms of anti-ZIKV activity of most of these drugs have not been elucidated. The limitations of these drugs make our findings especially important for further development of novobiocin into a clinically useful anti-ZIKV treatment option. Nevertheless, these drugs may still be useful for treating different groups of ZIKV-infected patients when used under special circumstances (e.g.: Cmax: $IC_{50}$ ratio of a 500 mg intravenous dose of azithromycin against ZIKV can be as high as 2.31). Further evaluation of their in vivo effects, alone or in combination, in animal models and clinical trials should be considered.

The successful identification of numerous ZIKV-NS2B-NS3 protease inhibitors among primary hit compounds and validation of novobiocin as a potent anti-ZIKV drug has demonstrated the capability of our combined in silico, in vitro, and in vivo platform to discover enzyme inhibitors of ZIKV among immediately available clinically approved drugs. The same approach should be considered for screening other large chemical libraries for potential ZIKV helicase or polymerase inhibitors to expand the treatment options for ZIKV infection.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Those skilled in the art will recognize, or be able to ascertain using no more than routine experimentation, many equivalents to the specific embodiments of the method and compositions described herein. Such equivalents are intended to be encompassed by the following claims.

We claim:

1. A method for treating Zika virus infection, the method comprising:
    administering, to a subject suffering from, or being at risk of developing, Zika virus infection, an effective amount of a composition that inhibits Zika virus protease,
    wherein the composition comprises novobiocin, rifampicin, desmopressin acetate, octreotide acetate, or any combination thereof.

2. The method of claim 1, wherein the amount of the composition is effective to inhibit Zika virus protease in the subject.

3. The method of claim 1, wherein the subject is an adult.

4. The method of claim 1, wherein the subject is pregnant.

5. The method of claim 1, wherein the subject is immune compromised.

6. The method of claim 1, wherein the composition comprises novobiocin and lopinavir-ritonavir.

7. The method of claim 1, wherein the composition comprises an effective amount of novobiocin, wherein the effective amount of novobiocin is less than 300 mg/kg/d.

8. The method of claim 1 further comprising, prior to administering, diagnosing the subject as suffering from, or being at risk of developing, Zika virus infection.

9. The method of claim 1, wherein the subject is suffering from Zika virus infection, wherein the amount of the composition administered to the subject is an amount effective to treat the Zika virus infection in the subject.

\* \* \* \* \*